US012590967B2

(12) United States Patent
Miyazawa et al.

(10) Patent No.: US 12,590,967 B2
(45) Date of Patent: Mar. 31, 2026

(54) METHOD FOR DETECTING PARTICULATE SUBSTANCE USING IMMUNOCHROMATOGRAPHY, AND KIT FOR SAME

(71) Applicants: DAI NIPPON TORYO CO., LTD., Osaka (JP); SHIMADZU CORPORATION, Kyoto (JP)

(72) Inventors: Yuta Miyazawa, Utsunomiya (JP); Daigou Mizoguchi, Nasushiobara (JP); Hirotaka Fujimoto, Kyoto (JP); Makoto Watanabe, Kyoto (JP); Taka-Aki Sato, Kyoto (JP)

(73) Assignees: DAI NIPPON TORYO CO., LTD, Osaka (JP); SHIMADZU CORPORATION, Kyoto (JP)

( * ) Notice: Subject to any disclaimer, the term of this patent is extended or adjusted under 35 U.S.C. 154(b) by 1035 days.

(21) Appl. No.: 17/640,032

(22) PCT Filed: Sep. 7, 2020

(86) PCT No.: PCT/JP2020/033823
§ 371 (c)(1),
(2) Date: Mar. 3, 2022

(87) PCT Pub. No.: WO2021/045229
PCT Pub. Date: Mar. 11, 2021

(65) Prior Publication Data
US 2022/0317128 A1 Oct. 6, 2022

(30) Foreign Application Priority Data
Sep. 6, 2019 (JP) ................................. 2019-163068

(51) Int. Cl.
*G01N 33/574* (2006.01)
*G01N 21/64* (2006.01)
(Continued)

(52) U.S. Cl.
CPC ... *G01N 33/57488* (2013.01); *G01N 21/6428* (2013.01); *G01N 21/76* (2013.01);
(Continued)

(58) Field of Classification Search
None
See application file for complete search history.

(56) References Cited

U.S. PATENT DOCUMENTS 4,855,240 A 8/1989 Rosenstein et al.
4,960,691 A 10/1990 Gordon et al.
(Continued)

FOREIGN PATENT DOCUMENTS

CN 108693347 A 10/2018
JP S63-96559 A 4/1988
(Continued)

OTHER PUBLICATIONS

Chen (J. Am. Chem. Soc. 2016 138:6356-6359). (Year: 2016).*
(Continued)

*Primary Examiner* — Changhwa J Cheu
(74) *Attorney, Agent, or Firm* — HAUPTMAN HAM, LLP

(57) ABSTRACT

The present invention relates to a method for detecting a particulate substance by immunochromatography, the particulate substance including, on its surface, a plurality of substances to be bound containing a first substance to be bound and a second substance to be bound which may be the same or different with respect to each other, wherein the method includes the steps of: (1) contacting on a membrane a sample containing the particulate substance with a first specific binding substance for the first substance to be bound to capture the particulate substance with the first specific binding substance; (2) contacting the captured particulate substance with a second specific binding substance for the
(Continued)

second substance to be bound to label the particulate substance; and (3) detecting the labeled particulate substance, wherein the first specific binding substance is immobilized on the membrane, and the second specific binding substance is bound to a metal nanoparticle.

20 Claims, 17 Drawing Sheets

(51) Int. Cl.

| | | |
|---|---|---|
| *G01N 21/76* | (2006.01) | |
| *G01N 21/77* | (2006.01) | |
| *G01N 33/543* | (2006.01) | |

(52) U.S. Cl.
CPC .................. *G01N 33/54388* (2021.08); *G01N 2021/6439* (2013.01); *G01N 2021/7759* (2013.01)

(56) References Cited

U.S. PATENT DOCUMENTS

| | | | |
|---|---|---|---|
| 5,310,650 A | 5/1994 | McMahon et al. | |
| 10,725,031 B1 * | 7/2020 | Barbosa | B01L 3/5023 |
| 2006/0205059 A1 | 9/2006 | Esfandiari | |
| 2007/0148781 A1 | 6/2007 | Esfandiari | |
| 2008/0318341 A1 | 12/2008 | Esfandiari | |
| 2010/0173397 A1 | 7/2010 | Esfandiari | |
| 2011/0151584 A1 | 6/2011 | Esfandiari | |
| 2012/0003727 A1 | 1/2012 | Esfandiari | |
| 2013/0224885 A1 | 8/2013 | Kato et al. | |
| 2014/0045172 A1 | 2/2014 | Esfandiari | |
| 2015/0056688 A1 | 2/2015 | Esfandiari | |
| 2015/0204868 A1 * | 7/2015 | Mehra | C07K 14/195 506/18 |
| 2017/0176418 A1 * | 6/2017 | Bohannon | G01N 33/54388 |
| 2017/0199185 A1 | 7/2017 | Miyazawa et al. | |
| 2019/0079087 A1 | 3/2019 | Miyazawa et al. | |
| 2021/0255179 A1 | 8/2021 | Miyazawa et al. | |

FOREIGN PATENT DOCUMENTS

| | | | | | |
|---|---|---|---|---|---|
| JP | S63-305252 A | | 12/1988 | | |
| JP | 2002-267671 A | | 9/2002 | | |
| JP | 2008-533472 A | | 8/2008 | | |
| JP | 2009-002822 A | | 1/2009 | | |
| JP | 2012-112042 A | | 6/2012 | | |
| JP | 2015-230280 A | | 12/2015 | | |
| JP | 2017-095744 A | | 6/2017 | | |
| JP | 2017-106915 A | | 6/2017 | | |
| JP | 2019-007984 A | | 1/2019 | | |
| JP | 2019-113425 A | | 7/2019 | | |
| JP | 2019-215176 A | | 12/2019 | | |
| KR | 2006-0109595 A | | 10/2006 | | |
| KR | 2018-0130640 A | | 12/2018 | | |
| WO | WO-2013036913 A1 * | | 3/2013 | ........ | G01N 33/6893 |
| WO | 2015/182770 A1 | | 12/2015 | | |
| WO | 2017/154989 A1 | | 9/2017 | | |
| WO | 2019/023597 A1 | | 1/2019 | | |

OTHER PUBLICATIONS

Ching et al. Chapter 13 "Lateral Flow Immunoassay" in Book "ELISA Methods and Protocols" 2015 edited by Robert Hnasko (Year: 2015).*

Jiang Adv. Healthcare Mater. 2019 8:1900244 (Year: 2019).*

Katis Biosensors and Bioelectronics 2018 113:95-100 (Year: 2018).*

Rong Analytica Chimica Acta 2019 1055: 140-147 (Year: 2019).*

M. Oliveira-Rodrigues et al., "Development of a rapid lateral flow immunoassay test for detection of exosomes previously enriched from cell culture medium and body fluids," Journal of Extracellular Vesicles 2016, 5:1, 31803, DOI: 10.3402/jev.v5.31803.

M. Oliveira-Rodrigues et al., "Point-of-care detection of extracellular vesicles: Sensitivity optimization and multiple-target detection," Biosensors and Bioelectronics 87 (2017) 38-45.

PCT/ISA/210, "International Search Report for International Application No. PCT/JP2020/033823," Nov. 24, 2020.

Japan Patent Office, "Office Action for Japanese Patent Application 2019-163068," Aug. 8, 2022.

European Patent Office, "Extended European Search Report with Search Opinion for European Patent Application 20860818.2," Aug. 28, 2023.

\* cited by examiner

Anti-CD9 antibody

METHOD FOR DETECTING PARTICULATE SUBSTANCE USING IMMUNOCHROMATOGRAPHY, AND KIT FOR SAME

RELATED APPLICATIONS

The present application is National Phase of International Application No. PCT/JP2020/033823 filed Sep. 7, 2020, and claims priority from Japanese Application No. 2019-163068, filed Sep. 6, 2019, the disclosure of which is hereby incorporated by reference herein in its entirety.

TECHNICAL FIELD

The present invention relates to a method for detecting a particulate substance using immunochromatography, as well as a test strip and a kit for immunochromatography for the same.

BACKGROUND ART

Particulate substances such as extracellular vesicles and viruses can be detected by immunochromatography (Patent Literature 1, as well as Non-Patent Literatures 1 and 2). Immunochromatography is a test method that enables more rapid detection compared with Western blotting and ELISA. This method is superior to measurements by NanoSight or the like, for example, in terms of capable of target detecting particulate substances without isolation, and capable of separately detecting particulate substances comprising specific non-detectable substances on their surfaces from other particulate substances. Further, exosomes which are extracellular vesicles are particulate substances that are contained in various body fluids such as breast milk, saliva, and tears in addition to blood and urine. Since exosomes are known to contain microRNA specific to cells, they have been attracting attention as target substances in cancer diagnosis using body fluids. Patent Literature 1, as well as Non-Patent Literatures 1 and 2 describe, as a method for detecting such an exosome, a method comprising: reacting the exosome with a labeling antibody to form a complex; and then developing the complex on a lateral flow membrane to bind the complex to a capture antibody which is immobilized on the membrane.

On the other hand, Patent Literatures 2 to 5 describe labeling substances such as various metal nanoparticles used for detecting a subject substance. However, these literatures fail to describe practically detecting particulate substances such as extracellular vesicles.

CITATION LIST

Patent Literature

Patent Literature 1: Japanese Patent Laid-Open No. 2015-230280
Patent Literature 2: International Publication No. WO/2015/182770
Patent Literature 3: Japanese Patent Laid-Open No. 2017-95744
Patent Literature 4: International Publication No. WO/2017/154989
Patent Literature 5: Japanese Patent Application No. 2018-111014

Non-Patent Literature

Non Patent Literature 1: Journal of Extracellular Vesicles (2016), 5:1, 31803, DOI: 10.3402/jev.v5.31803

Non-Patent Literature 2: Biosensors and Bioelectronics (2017), 87, 38-45

SUMMARY OF INVENTION

Problem to be Solved by the Invention

In conventional immunochromatography, its detection sensitivity has not been sufficient because the surface of a particulate substance is covered by a labeling antibody before the particulate substance is developed on a membrane, which results in reducing the reactivity with a capture antibody. The purpose of the present invention is to provide a method for detecting a particulate substance with high sensitivity.

Means for Solution of the Problem

As a result of diligent study to solve the foregoing problem, the present inventors found out that a particulate substance can be detected with high sensitivity, by performing immunochromatography in specific order, and accomplished the present invention. In other words, the present invention provides a method for detecting a particulate substance set forth below by immunochromatography, as well as a test strip and a kit for immunochromatography for the same.

{1} A method for detecting a particulate substance by immunochromatography, the particulate substance comprising, on its surface, a plurality of substances to be bound containing a first substance to be bound and a second substance to be bound which may be the same or different with respect to each other, wherein the method comprises the steps of:

(1) contacting on a membrane a sample containing the particulate substance with a first specific binding substance for the first substance to be bound to capture the particulate substance with the first specific binding substance;

(2) contacting the captured particulate substance into contact with a second specific binding substance for the second substance to be bound to label the particulate substance; and (3) detecting the labeled particulate substance, wherein the first specific binding substance is immobilized on the membrane, and the second specific binding substance is bound to a labeling substance.

{2} The method according to {1}, wherein the particulate substance is an extracellular vesicle.

{3} The method according to {1} or {2}, wherein the labeling substance is a metal nanoparticle, a chemiluminescence substance, or a luminescence substance.

{4} The method according to {3}, wherein the metal nanoparticle is an anisotropic metal nanoparticle.

{5} The method according to {4}, wherein the anisotropic metal nanoparticle is blue or black, and the sample contains blood.

{6} The method according to any one of {1} to {5}, further comprising the step of adding a surfactant to the sample.

{7} The method according to any one of {1} to {6} wherein the first substance to be bound is the same as the second substance to be bound.

{8} The method according to {7}, wherein the binding site of the first specific binding substance in the first substance to be bound is the same as the binding site of the second specific binding substance in the second substance to be bound.

{9} The method according to any one of {1} to {8}, wherein the detecting step comprises the step of quantifying the particulate substance.

{10} The method according to {9}, wherein the quantifying step comprises the step of measuring a labeling signal by a mass spectrometer, an immunochromatography reader, or an image analyzer.

{11} The method according to {10}, wherein an ionization method of the mass spectrometer is an Inductively Coupled Plasma (ICP) method or a Matrix-Assisted Laser Desorption/Ionization (MALDI) method.

{12} A test strip for immunochromatography to use in the method according to any one of {1} to {11}.

{13} A kit for detecting a particulate substance by the method according to any one of {1} to {11}, the particulate substance comprising, on its surface, a plurality of substances to be bound containing a first substance to be bound and a second substance to be bound which may be the same or different with respect to each other, wherein the kit comprises:

a test strip including a membrane;

a first specific binding substance for the first substance to be bound; and a second specific binding substance for the second substance to be bound, wherein the first specific binding substance is immobilized on the membrane, and the second specific binding substance is bound to a labeling substance.

{14} A test strip for immunochromatography to detect a particulate substance, the particulate substance comprising, on its surface, a plurality of substances to be bound containing a first substance to be bound and a second substance to be bound which may be the same or different with respect to each other, wherein the test strip comprises:

a membrane comprising a detection site where a first specific binding substance for the first substance to be bound is immobilized;

a first sample pad contacting the membrane in the upstream-side position of the detection site with respect to a sample flowing direction, wherein no conjugate pad is included on the way from the first sample pad to the detection site.

{15} The test strip according to {14}, further comprising a second sample pad contacting the membrane in the far upstream-side position of the first sample pad with respect to the sample flowing direction, wherein the second sample pad is spaced from the first sample pad.

{16} The test strip according to {15}, wherein the second sample pad comprises a conjugate pad containing a second specific binding substance for the second substance to be bound, and the second specific binding substance is bound to a labeling substance.

{17} The test strip according to {15} or {16}, wherein the first sample pad and the second sample pad are spaced from each other via a first spacer.

{18} The test strip according to any one of {15} to {17}, wherein the membrane is configured so as to inhibit the penetration of a sample containing the particulate substance from the first sample pad-side into the second sample pad-side.

{19} The test strip according to any one of {15} to {18}, wherein the particulate substance further comprises a third substance to be bound which may be the same as or different from the first substance to be bound or the second substance to be bound, wherein the membrane further comprises: an additional detection site where a third specific binding substance for the third substance to be bound is immobilized; and a second spacer arranged so as to divide a route in which the sample is flowing in the downstream-side position of the first sample pad, and wherein the detection site and the additional detection site are arranged in different routes which are divided by the second spacer.

{20} A test strip for immunochromatography to detect a particulate substance, the particulate substance comprising, on its surface, a plurality of substances to be bound containing a first substance to be bound and a second substance to be bound which may be the same or different with respect to each other, wherein the test strip comprises:

a membrane comprising a detection site where a first specific binding substance for the first substance to be bound is immobilized;

a first substrate which includes a first sample pad contacting the membrane in the upstream-side position of the detection site with respect to a sample flowing direction; and a second substrate which includes a second sample pad, wherein the first substrate and the second substrate are approachable so that the second sample pad contacts the membrane in the far upstream-side position of the first sample pad with respect to the sample flowing direction.

{21} The test strip according to {20}, wherein the second sample pad comprises a conjugate pad containing a second specific binding substance for the second substance to be bound, and the second specific binding substance is bound to a labeling substance.

{22} The test strip according to {20} or {21}, wherein the first substrate and the second substrate are bound via an expandable structure.

{23} A test strip for immunochromatography to detect a particulate substance, the particulate substance comprising, on its surface, a plurality of substances to be bound containing a first substance to be bound and a second substance to be bound which may be the same or different with respect to each other, wherein the test strip comprises:

a membrane comprising a detection site where a first specific binding substance for the first substance to be bound is immobilized;

a first sample pad contacting the membrane in the upstream-side position of the detection site with respect to a sample flowing direction in a first route; and a second sample pad contacting the membrane in the upstream-side position of the detection site with respect to a sample flowing direction in a second route which is different from the first route, wherein the second sample pad is spaced from the first sample pad.

{24} The test strip according to {23}, wherein the second sample pad comprises a conjugate pad containing a second specific binding substance for the second substance to be bound, and the second specific binding substance is bound to a labeling substance.

{25} The test strip according to {23} or {24}, wherein the membrane is strip-shaped, U-shaped, or V-shaped.

{26} The test strip according to {23} or {24}, wherein the particulate substance comprises a third substance to be bound which may be the same as or different from the first substance to be bound or the second substance to be bound, wherein the membrane further comprises: an additional detection site where a third specific binding substance for the third substance to be bound is immobilized; and a spacer arranged so as to divide the first route in the downstream-side position of the first sample pad with respect to a sample flowing direction in the first route, and wherein the detection site and the additional detection site are arranged in different routes which are divided by the spacer.

{27} The test strip according to {26}, further comprising a third sample pad contacting the membrane in the upstream-side position of the additional detection site with respect to a sample flowing direction in a third route which is different from the first route and the second route.

{28} The test strip according to {27}, wherein the second sample pad and/or the third sample pad comprises a conjugate pad containing the second specific binding substance.

{29} A test strip for immunochromatography to detect a particulate substance, the particulate substance comprising, on its surface, a plurality of substances to be bound containing a first substance to be bound and a second substance to be bound which may be the same or different with respect to each other, wherein the test strip comprises:

a first membrane comprising a detection site where a first specific binding substance for the first substance to be bound is immobilized;

a first sample pad contacting the first membrane in the upstream-side position of the detection site with respect to a sample flowing direction in a first route;

a second membrane contacting the first membrane between the detection site and the first sample pad; and a second sample pad contacting the second membrane in the upstream-side position of the detection site with respect to a sample flowing direction in a second route which is different from the first route, wherein the second sample pad is spaced from the first sample pad.

{30} The test strip according to {29}, wherein either one of the first sample pad or the second sample pad comprises a conjugate pad containing a second specific binding substance for the second substance to be bound, and the second specific binding substance is bound to a labeling substance.

{31} The test strip according to any one of {14} to {30}, further comprising a control site where the success or failure of an immunochromatography test is judged.

Advantageous Effects of Invention

According to the present invention, the detection sensitivity of a particulate substance in immunochromatography can be improved. Therefore, immunochromatography allows a particulate substance to be detected in a quick and highly sensitive manner.

BRIEF DESCRIPTION OF DRAWINGS

FIG. 22 shows the result of Western blotting for exosome solutions.

DESCRIPTION OF EMBODIMENTS

Figure 1:
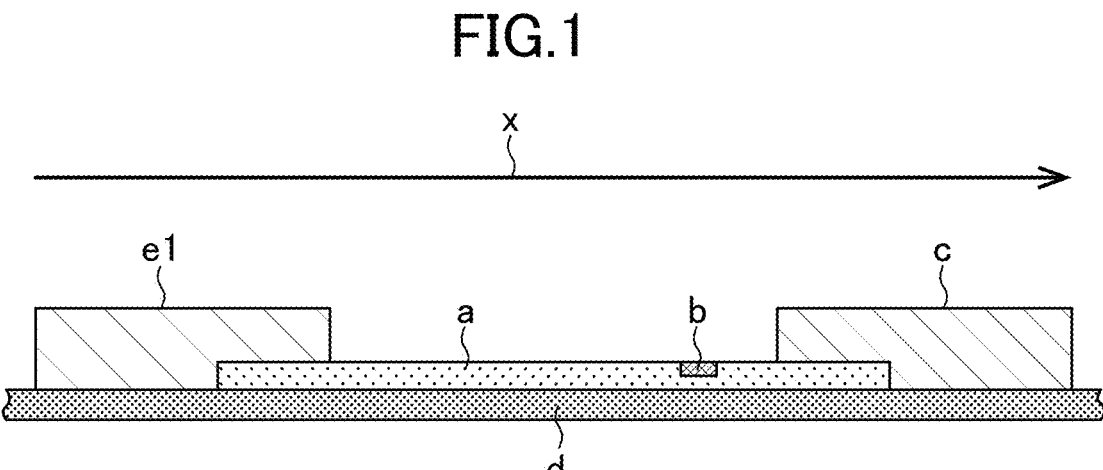
FIG. 1 shows one aspect of a test strip of the present invention for immunochromatography.

In the following, the present invention is described in more detail.

The present invention relates to a method for detecting a particulate substance by immunochromatography. "Immunochromatography" described in the present specification is a method for detecting a target substance in a sample using a substance that specifically binds to the substance, and refers not only to a lateral flow detection method that separates the target substance by moving the sample on the membrane, but also to a flow-through (vertical flow) detection method that separates the target substance by moving the sample vertically with respect to the membrane. The "particulate substance" described in the present specification refers to a particulate substance having a size that can be detected by immunochromatography. The particulate substance comprises, on its surface, a plurality of at least one kind of substance to be bound. The substances to be bound include a first substance to be bound and a second substance to be bound that may be the same or different from each other. The particle size of the particulate substance is not particularly limited, but may be, for example, about 10 μm or less, or in an aspect, about 5 μm or less, about 1 μm or less, about 500 nm or less, or about 200 nm or less. Specifically, the particulate substance may be, for example, extracellular vesicles, such as exosomes, microvesicles, apoptotic bodies, and large oncosomes; viruses, such as influenza virus, adenovirus, RS virus, rotavirus, human papillomavirus, human immunodeficiency virus, hepatitis B virus, Zika virus, and dengue virus; or bacteria, such as *chlamydia, Treponema pallidum*, streptococcal, anthrax, *Staphylococcus aureus, Shigella, Escherichia coli, Salmonella, Salmonella Typhimurium, Salmonella* Paratyphi, *Pseudomonas aeruginosa*, and *Vibrio parahaemolyticus*.

Any sample containing the particulate substance can be used without particular limitation as long as it can be subjected to immunochromatography. As a sample to be applied to the method of the present invention, a sample collected from a living body or a culture medium may be used as is, or a sample that is purified, partially purified, or concentrated by pretreatment, such as filtration or centrifugation, may be used. Specifically, the sample include body fluids, such as blood (whole blood, serum, or plasma), cerebral spinal fluid, tears, breast milk, alveolar lavage fluid, malignant pleural effusion, synovial fluid, urine, amniotic fluid, ascites, semen, saliva, and lymph; preservative solutions for tissue sections, cell culture supernatants, and the like.

A method of the present invention comprises the steps of:

(1) contacting on a membrane a sample containing the particulate substance with a first specific binding substance for a first substance to be bound to capture the particulate substance with the first specific binding substance;

(2) contacting the captured particulate substance with a second specific binding substance for the second substance to be bound to label the particulate substance; and (3) detecting the labeled particulate substance. When the first substance to be bound and the second substance to be bound are the same, the binding site of the first specific binding substance in the first substance to be bound may be the same as or different from the binding site of the second specific binding substance in the second substance to be bound. Even when both binding sites are the same, the particulate substance has a plurality of substances to be bound on its surface, which allows labeling it with the second specific binding substance after it is captured by the first specific binding substance as well.

The first specific binding substance is immobilized on the membrane, and can capture the particulate substance having the first substance to be bound on the membrane. As the membrane, any membrane can be used without particular limitation as long as it is used as a test strip for immunochromatography (immunochromatography test paper) (i.e., a membrane that has the ability to immobilize the first specific binding substance, and that does not prevent liquid from passing in the desired direction). For example, the membrane may be a porous membrane having capillarity and capable of transporting liquid and components dispersed therein by absorption. The material of the membrane is not particularly limited, but may be, for example, cellulose, nitrocellulose, cellulose acetate, polyvinylidene fluoride (PVDF), glass fiber, nylon, polyketone, or the like.

As the first specific binding substance, any substance can be adopted without particular limitation as long as it can be immobilized on the membrane and can capture the particulate substance to be detected on the membrane through the formation of a complex with the first substance to be bound. Specific examples of combinations of the first substance to be bound and the first specific binding substance include an antigen and an antibody that binds thereto, an antibody and an antigen that binds thereto, a sugar chain or complex carbohydrate and a lectin that binds thereto, a lectin and a sugar chain or complex carbohydrate that binds thereto, a hormone or cytokine and a receptor that binds thereto, a receptor and a hormone or cytokine that binds thereto, a protein and a nucleic acid aptamer or peptide aptamer that binds thereto, an enzyme and a substrate that binds thereto, a substrate and an enzyme that binds thereto, biotin and avidin or streptavidin, avidin or streptavidin and biotin, IgG and protein A or protein G, protein A or protein G and IgG, T-cell immunoglobulin and mucin domain-containing molecule 4 (Tim 4) and phosphatidylserine (PS), PS and Tim 4, or a first nucleic acid and a second nucleic acid that binds (hybridizes) thereto, and the like. The second nucleic acid may be a nucleic acid containing a sequence complementary to the first nucleic acid.

When the first substance to be bound is an antigen, the first specific binding substance may be an antibody. Specifically, when the particulate substance is an exosome, the first substance to be bound may be CD9, CD63, or CD81, and the first specific binding substance may be anti-CD9 antibody, anti-CD63 antibody, or anti-CD81 antibody. The antibody may be a polyclonal antibody, a monoclonal antibody, a single-chain antibody, or a fragment thereof, all of which specifically bind to the antigen. The fragment may be an F(ab) fragment, an F(ab') fragment, an $F(ab')_2$ fragment, or an F(v) fragment.

The second specific binding substance binds to a labeling substance, and can label a particulate substance having the second substance to be bound. The second specific binding substance and the labeling substance may be combined to form a complex, regardless of the mode of binding, such as covalent bond or non-covalent bond or direct or indirect bond. As the second specific binding substance, any substance can be adopted without particular limitation as long as the particulate substance to be detected can be detected by the formation of a complex with the second substance to be bound. Specific examples of combinations of the second substance to be bound and the second specific binding substance include the same as the specific examples of combinations of the first substance to be bound and the first specific binding substance described above.

The "labeling substance" described herein refers to a substance that provide a mark when the bind between the second specific binding substance and the second substance to be bound are detected. The labeling substance is not specifically limited, but may be a metal nanoparticle, a chemiluminescence substance and a fluorescence substance, for example. The "metal nanoparticle" described herein refers to a particle that is produced by metal and has a size on the order of nanometers (nm). The metal is not specifically limited, but may be gold or silver. The metal nanoparticle is not specifically limited, but may be an anisotropic metal nanoparticle or a spherical metal nanoparticle. The "anisotropic metal nanoparticle" as set forth herein refers to a metal nanoparticle whose shape is anisotropic, i.e., a metal nanoparticle which is not spherical. The shape of the anisotropic metal nanoparticle is not limited, but may be polyhedral, cubic, double metal ball-shaped, bar-shaped (rod-shaped), or board-shaped (plate-shaped). When the shape of the anisotropic metal nanoparticle is board-shaped, its top and bottom shape has a board-shaped structure such as a polygon such as a triangle, a quadrangle, a pentagon, a hexagon (including a shape with rounded corners), or a circle.

The surface of the metal nanoparticle may be coated with an additional metal. The combination of the metal and the additional metal is not specifically limited as long as the formed metal nanoparticle with coating bears the second specific binding substance and can be used as a label. For example, when the metal is gold, the additional metal may be palladium, and when the metal is silver, the additional metal may be gold.

An index defined by the ratio between the longest diameter and the width perpendicular to the longest diameter of a particle (the longest diameter/the width perpendicular to the longest diameter; for example, in the case of a bar-shaped particle, its major axis/its minor axis, and in the case of a board-shaped particle, its planar maximum length/its thickness) is referred to as an aspect ratio, and this index can be used for representing the shape of particles. When the shape of the metal nanoparticle changes, the position of its maximum absorption wavelength also changes, and thus the aspect ratio can be said as an index for the maximum absorption wavelength. The aspect ratio of the anisotropic metal nanoparticle is larger than 1.00. The aspect ratio of larger than 1 allows the anisotropic metal nanoparticle to express a tone that cannot be achieved by a spherical metal nanoparticle. For example, the anisotropic metal nanoparticle can express a tone of red, magenta, purple, navy blue, blue, cyan or pale blue. With the use of a metal nanoparticle which express a tone which is easy to distinguish it from the tone of a sample and a membrane, it is advantageous to detect the particulate substance. For example, when a sample containing the particulate substance contains blood, the use of a blue or black metal nanoparticle is preferable.

As the metal nanoparticle, a commercially available metal nanoparticle, or a metal nanoparticle which is produced by a known method usually adopted in the metal nanoparticle field can be used (see Patent Literatures 1 to 5, as well as non-Patent Literatures 1 and 2 and the like, if necessary).

The "chemiluminescence substance" described in the present specification refers to a substance involved in the chemical reaction that produces photons. Examples thereof include chemiluminescence enzyme that catalyzes the chemical reaction. The chemiluminescence enzyme is not particularly limited, and may be, for example, peroxidases such as horseradish peroxidase (HRP), alkaline phosphatase, or luciferase. The peroxidases catalyze the reaction of luminol-based compounds, the alkaline phosphatase catalyzes the reaction of dioxetane-based compounds, and the luciferase catalyzes the reaction of luciferin-based compounds.

The "fluorescence substance" described in the present specification refers to a substance that absorbs excitation light and emits fluorescence. The fluorescence substance is not particularly limited, and may be, for example, fluorescein isothiocyanate (FITC), phycoerythrin (PE), allophycocyanin (APC), or a derivative thereof.

As the method for binding the second specific binding substance and the labeling substance, general binding methods can be used without particular limitation. Usable examples include methods for directly binding the labeling substance to the second specific binding substance using physical adsorption, chemical adsorption (covalent bond to the surface), chemical bond (covalent bond, coordination bond, ionic bond, or metal bond), or the like; and methods for directly or indirectly binding the second specific binding substance to the terminal, main chain, or side chain of a water-soluble polymer bound to the surface of the labeling substance. For example, when the second specific binding substance is an antibody, and the labeling substance is a metal nanoparticle, a solution for the metal nanoparticle and a solution for the antibody can be mixed, shaken, and centrifuged to obtain the metal nanoparticle bound to the antibody (the labeled detection antibody) as a precipitate. When the metal nanoparticle and the antibody are bound by electrostatic adsorption, coating the surface of the metal nanoparticle with polystyrene sulfonate having a negative charge can improve the binding efficiency of the antibody. Also, when the labeling substance is a chemiluminescence enzyme, an activation ester is introduced into the enzyme to react with the second specific binding substance to bind both of them.

While not wishing to be bound by any particular theory, in a conventional method in which a particulate substance is labeled with an antibody and then it is captured by an antibody on a membrane, the labeling antibody previously bound to the particulate substance may inhibit the capture antibody from binding. In contrast, it is believed that the method of the present invention which comprises the (1) capturing process, followed by the (2) labeling process and the (3) detection process, allows the particulate substance to be captured on a membrane efficiently, thereby increasing the detection sensitivity as well. It is believed that since the particulate substance has a plurality of substances to be bound on its surface, one of them is able to provide a binding site to the first specific binding substance on its membrane side, and the other is able to provide a binding site to the second specific binding substance on its other side which is opposite to the membrane side.

In one aspect, the method of the present invention can further comprise the step of adding a surfactant to the sample. The surfactant is not specifically limited, but may be (octylphenoxy) polyethoxyethanol, 4-nonylphenyl-polyethylene glycol, polysorbate 20 (Tween® 20), polysorbate 60 (Tween® 60), polysorbate 80 (Tween® 80), sodium dodecyl sulfate or dodecylbenzenesulfonic acid sodium, for example. While not wishing to be bound by any particular theory, it is believed that, by adding a surfactant to the sample, the particulate substances are separated from each other to facilitate binding with the first specific binding substance or the second specific binding substance, resulting in allowing increase in the detection sensitivity of the particulate substance.

In the detection process of the present invention, the labeling substance aggregated at the detection site can be detected visually or using a detection device, either directly or by causing a chemical reaction or irradiation with excitation light. The detection device is not particularly limited. For example, a mass spectrometer, Immunochromato reader, or an image analyzer including a CCD imager, a scanner, image processing software, etc. may be used. Specifically, when the labeling substance is HRP, a substrate solution containing luminol, hydrogen peroxide, an enhancer, and the like is added dropwise on immunochromatography test paper after the immunochromatography test, and the resulting luminescence can be detected by an X-ray film or a CCD imager.

In an aspect, the detection process may include the step of quantifying the particulate substance. For example, for a standard sample whose content of the particulate substance has been clarified by measurement with a NanoSight nanoparticle analysis system or the like, a calibration curve may be created based on the difference in brightness determined with a scanner, image processing software, etc., or the absorbance measured with Immunochromato reader to determine the content of the particulate substance in an unknown sample. Alternatively, the judgment portion of immunochromatography test paper after the immunochromatography test may be cut into pieces, and metal which is bound thereto as a label is dissolved in aqua regia and the like to measure the metal concentration in the solution by a mass spectrometer. An ionization method of the mass spectrometer is not specifically limited, but may be an Inductively Coupled Plasma (ICP) method or a Matrix-Assisted Laser Desorption/Ionization (MALDI) method.

The method of the present invention may further comprise any step which is commonly used in the art as long as the purpose is not compromised. For example, the method of the present invention may comprise the step of isolating or purifying the particulate substance.

In another aspect, the present invention also relates to a kit for detecting a particulate substance by the method described above, the particulate substance comprising, on its surface, a plurality of substances to be bound containing a first substance to be bound and a second substance to be bound which may be the same or different with respect to each other, wherein the kit comprises: a test strip including a membrane; a first specific binding substance for the first substance to be bound; and a second specific binding substance for the second substance to be bound, wherein the first specific binding substance is immobilized on the membrane, and the second specific binding substance is bound to a labeling substance.

In a further aspect, the present invention also relates to a test strip for immunochromatography (immunochromatography test paper) used for a method for detecting the particulate substance by immunochromatography. The test strip is not specifically limited as long as the method can be performed, and may be a test strip used in lateral flow immunochromatography or a test strip used in flow-through (vertical flow) immunochromatography. As a simple test strip, it can be made by fixing a membrane and a water absorption pad to a backing sheet. Specifically, a strip-shaped test strip for immunochromatography (immunochromatography test paper) can be made by affixing a nitrocellulose membrane (25 mm long and 300 mm wide; made by TOYO ROSHI KAISHA, Ltd., IAB120) to a backing sheet (40 mm long and 300 mm wide; made by Lohmann, GL-57888) whose bottom end is aligned with the membrane, and further affixing a water absorption pad (20 mm long and 300 mm wide; made by Ahlstrom, Grade 0270) so as to overlap the top end of the nitrocellulose membrane by 5 mm, and finally cutting this into pieces in the 4 mm interval laterally. The first specific binding substance is immobilized around the center of the membrane, in accordance with an ordinary method. The test strip thus made can be used by immersing in a developing solution one side of the membrane where the water absorption pad has not been affixed.

Figure 2:
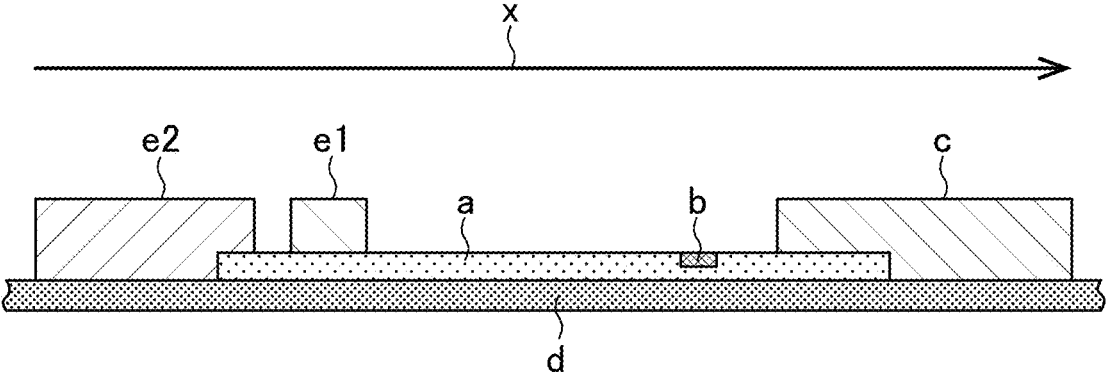
FIG. 2 shows one aspect of a test strip of the present invention for immunochromatography.

In another aspect, the present invention also relates to a test strip for immunochromatography (immunochromatography test paper) having a suitable shape for using a method for detecting the particulate substance by immunochromatography, i.e., to a test strip for immunochromatography for detecting a particulate substance comprising, on its surface, a plurality of target substances to be bound containing a first substance to be bound and a second substance to be bound which may be the same or different with respect to each other. Specifically, the test strip of the present invention for immunochromatography comprises:

a membrane (a) comprising a detection site (b) where a first specific binding substance for the first substance to be bound is immobilized; and a first sample pad (e1) contacting the membrane (a) in the upstream-side position of the detection site (b) with respect to a sample flowing direction (x), wherein no conjugate pad is included on the way from the first sample pad (e1) to the detection site (b), and each component can be arranged on a substrate (backing sheet) (d) (FIG. 1). The test strip may further include a water absorption pad (c) in the downstream-side position of the detection site (b) with respect to the sample flowing direction (x). Also, the test strip may further include a second sample pad (e2) contacting the membrane (a) in the far upstream-side position of the first sample pad (e1) with respect to the sample flowing direction, wherein the second sample pad (e2) is spaced from the first sample pad (e1) (FIG. 2).

The "sample pad" described herein refers to a site where a sample, a detection reagent, or a solvent such as water and a buffer for immunochromatography is received to start development (flow) on the membrane (a). The sample pad can be made by any method which is commonly used in the art. When the test strip of the present invention for immunochromatography includes only one sample pad, in other words, the first sample pad (e1) only, a sample containing the particulate substance is loaded onto this first sample pad (e1) to react the particulate substance with the first specific binding substance at the detection site (b), and then a detection reagent containing a second specific binding substance (binding to a labeling substance) for the second substance to be bound is loaded onto the same first sample pad (e1) to label the particulate substance captured in the detection site (b). When the test strip of the present invention for immunochromatography includes the first sample pad (e1) and the second sample pad (e2), the first sample pad (e1) may be used as a site for loading a sample containing the particulate substance, and the second sample pad (e2) may be used as a site for loading a detection reagent containing the second specific binding substance.

Figure 3:
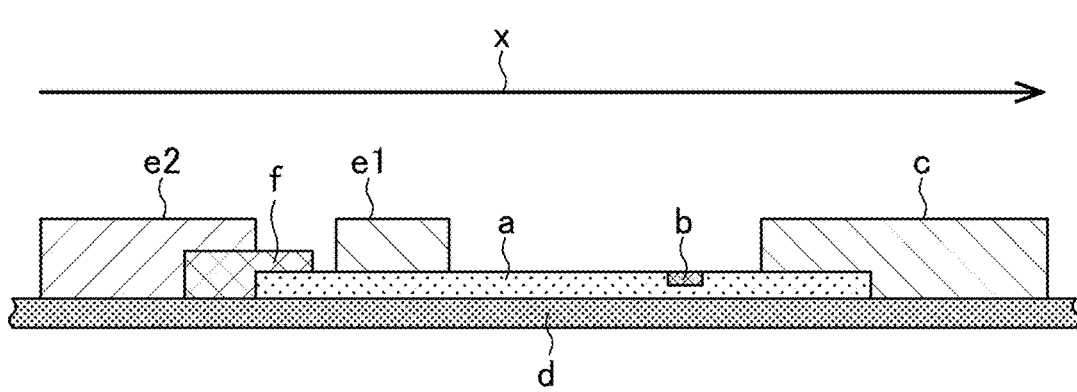
FIG. 3 shows one aspect of a test strip of the present invention for immunochromatography.

In one aspect, the second sample pad (e2) comprises a conjugate pad (f) containing the second specific binding substance (FIG. 3). The "conjugate pad" described herein is a site into which the second specific binding substance is impregnated, and is configured so as to, when a solvent such as water and a buffer is added thereto, elute the second specific binding substance to start development (flow) on the membrane (a). The conjugate pad (f) can be made by any method which is commonly used in the art. The conjugate pad (f) may have an aspect which is at least partly covered by the second sample pad (e2), or may have an aspect which is integrally formed with the second sample pad (e2), or may form an area which functions as the second sample pad (e2) along with another sample pad member arranged side by side.

Figure 4:
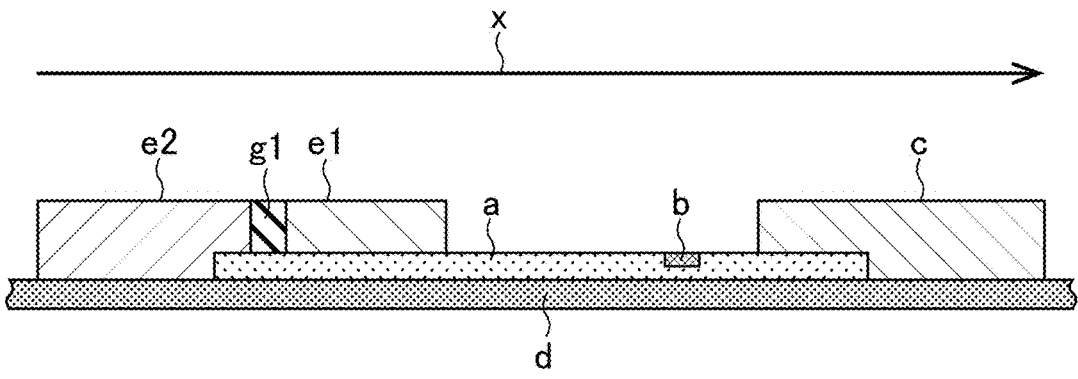
FIG. 4 shows one aspect of a test strip of the present invention for immunochromatography.
Figure 5:
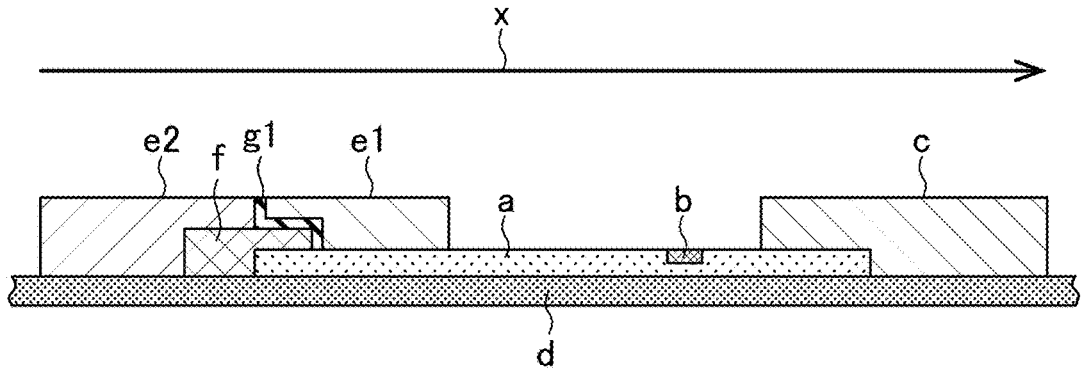
FIG. 5 shows one aspect of a test strip of the present invention for immunochromatography.

In one aspect, the first sample pad (e1) and the second sample pad (e2) are spaced from each other via a first spacer (g1) (FIGS. 4 and 5). Also, in one aspect, the membrane is configured so as to inhibit the penetration of a sample containing the particulate substance from the first sample pad-side into the second sample pad-side. As such a penetration inhibiting means, any means which is commonly used in the art can be adopted without particular limitation. For example, such a means may be configured so as to provide an inhibition area (h) where a water-soluble polymer is impregnated in the membrane (a) to reduce the flowing speed which is opposite to the sample flowing direction (x) (FIGS. 6 and 7).

Figures 6, 7, 8:
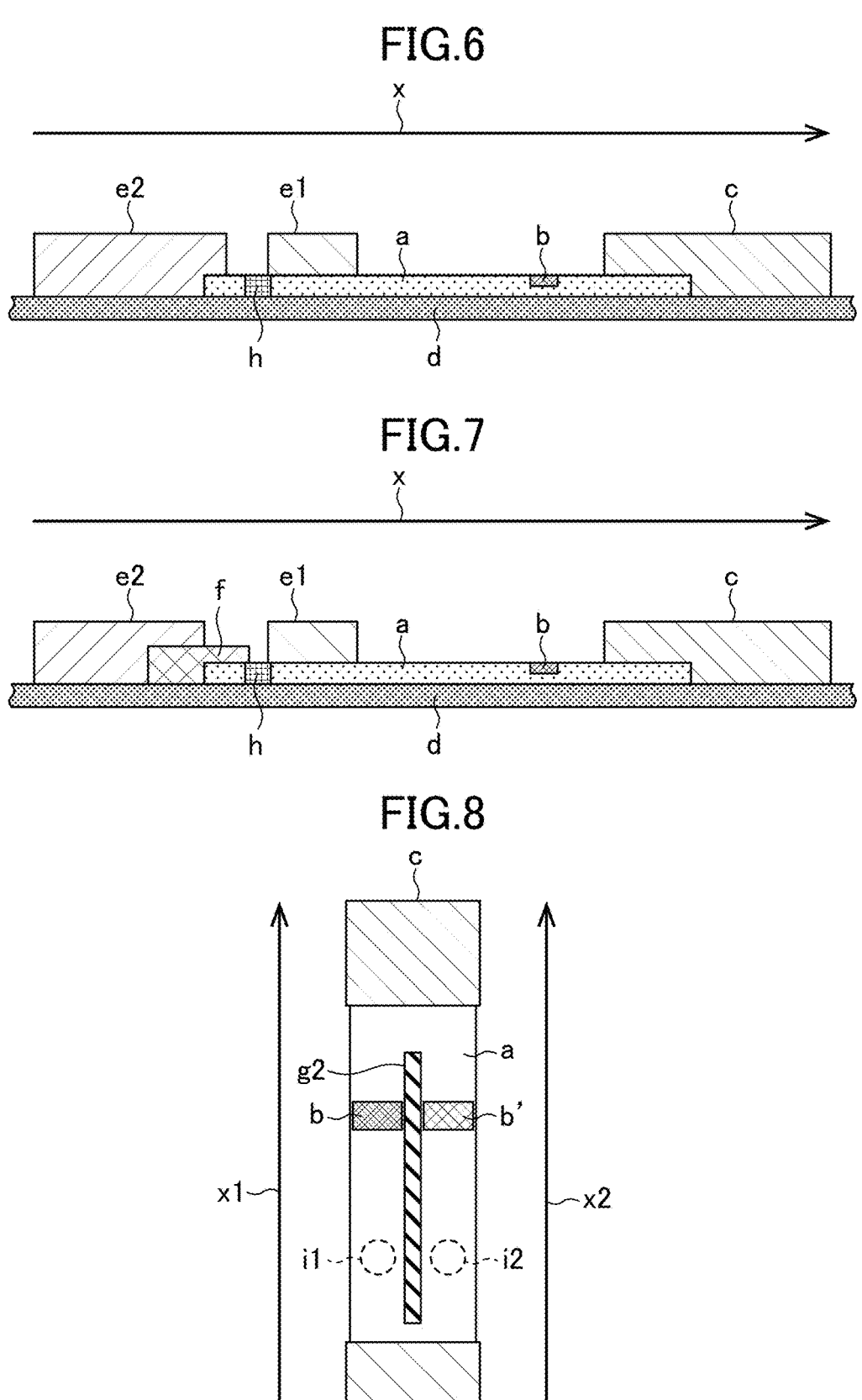
FIG. 6 shows one aspect of a test strip of the present invention for immunochromatography.
FIG. 7 shows one aspect of a test strip of the present invention for immunochromatography.
FIG. 8 shows one aspect of a test strip of the present invention for immunochromatography.

In one aspect, the particulate substance further comprises a third substance to be bound which may be the same as or different from the first substance to be bound or the second substance to be bound, wherein the membrane (a) further comprises: an additional detection site (b') where a third specific binding substance for the third substance to be bound is immobilized; and a second spacer (g2) arranged so as to divide a route in which the sample is flowing in the downstream-side position of the first sample pad, and wherein the detection site (b) and the additional detection site (b') are arranged in different routes which are divided by the second spacer (g2) (FIG. 8). When the first substance to be bound and the third substance to be bound are different, comparison of the amount of the particulate substance captured in the detection site (b) and the amount of the particulate substance captured in the additional detection site (b') allows the relative amount to be measured between the first substance to be bound and the third substance to be bound on the particulate substance in the sample. Meanwhile, it is also possible to detect the particulate substance captured in the detection site (b) and the particulate substance captured in the additional detection site (b') with different detection reagents, and in that case, the different detection reagents are respectively added dropwise to a first drop area (i1) which lies immediately above the detection site (b) or between the detection site (b) and the first sample pad (e1), and a second drop area (i2) which lies immediately above the additional detection site (b') or between the additional detection site (b') and the first sample pad (e1).

Figure 9:
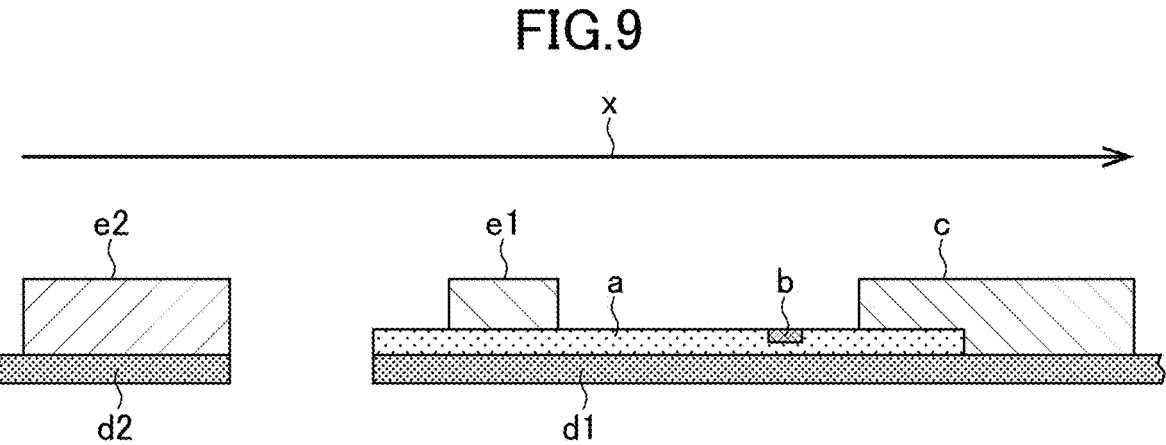
FIG. 9 shows one aspect of a test strip of the present invention for immunochromatography.

In another specific example, the test strip of the present invention for immunochromatography comprises:

a membrane (a) comprising a detection site (b) where a first specific binding substance for the first substance to be bound is immobilized;

a first substrate (d1) which includes a first sample pad (e1) contacting the membrane (a) in the upstream-side position of the detection site (b) with respect to a sample flowing direction (x); and a second substrate (d2) which includes a second sample pad (e2), wherein the first substrate (d1) and the second substrate (d2) are approachable so that the second sample pad (e2) contacts the membrane (a) in the far upstream-side position of the first sample pad (e1) with respect to the sample flowing direction (x) (FIG. 9). After a sample containing the particulate substance is flowed from the first sample pad (e1), the second sample pad (e2) can be brought into contact with the membrane (a) to flow a detection reagent containing a second specific binding substance (binding to a labeling substance) for the second substance to be bound from the second sample pad (e2) to label the particulate substance captured in the detection site (b).

Figure 10:
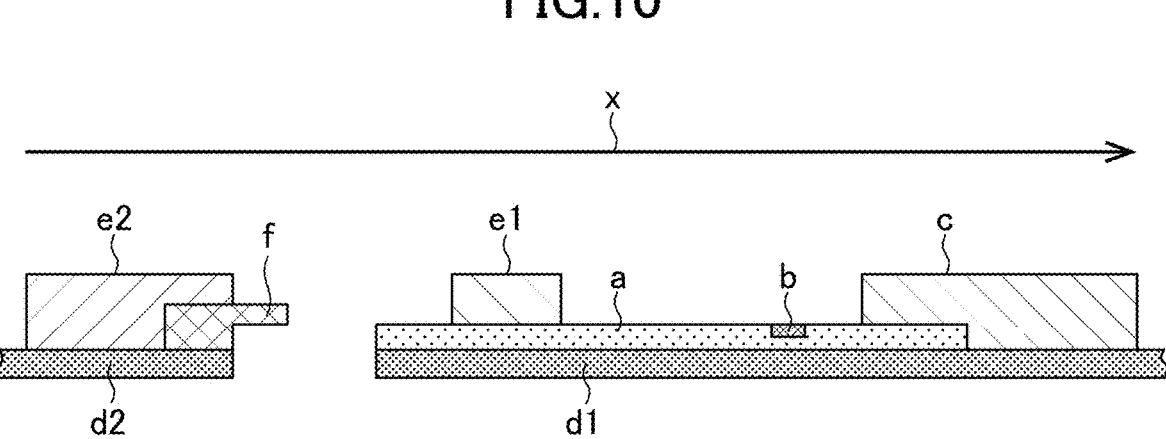
FIG. 10 shows one aspect of a test strip of the present invention for immunochromatography.
Figure 11:
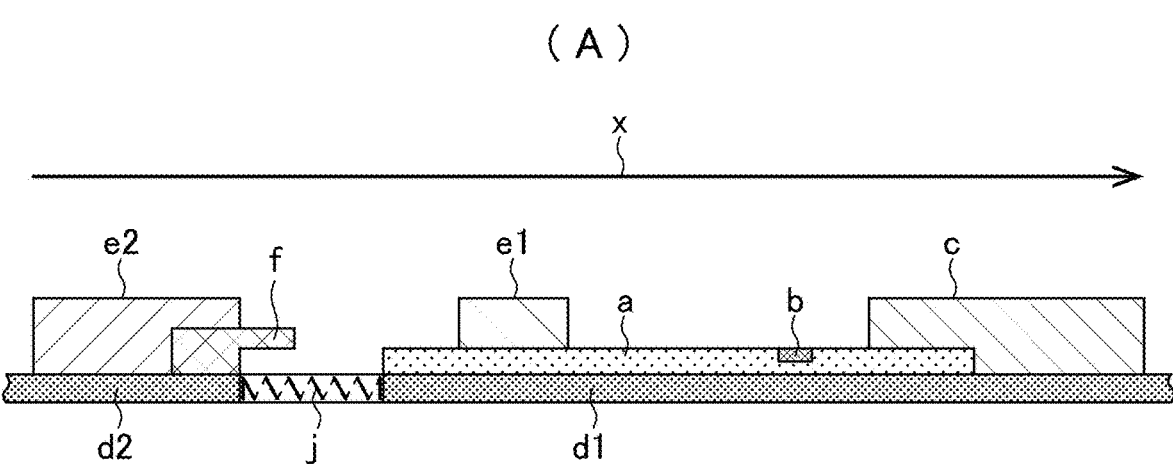
FIG. 11 shows one aspect of a test strip of the present invention for immunochromatography [(A) expansion and (B) contraction].
Figure 11:
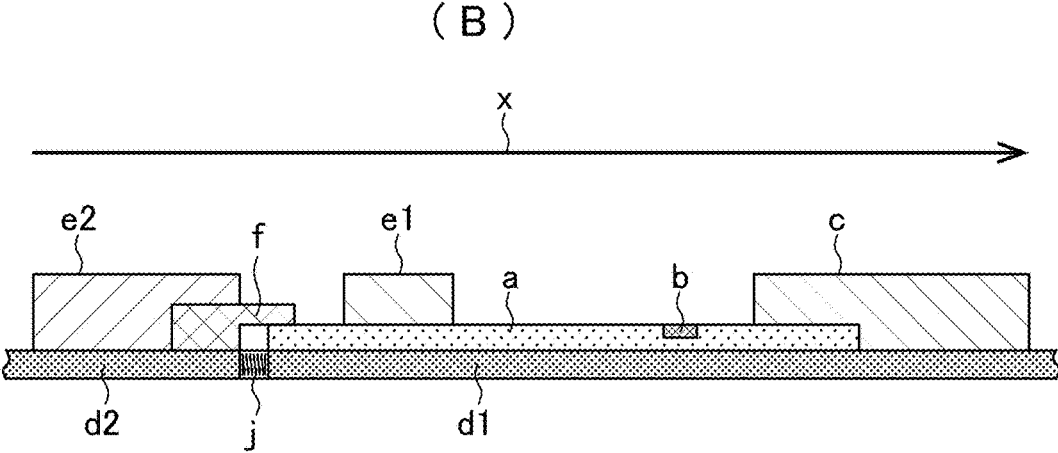

In one aspect, the second sample pad (e2) comprises a conjugate pad (f) containing the second specific binding substance (FIG. 10). Moreover, in one aspect, the first substrate (d1) and the second substrate (d2) are coupled via an expandable structure (j) (FIG. 11). In this case, a sample containing the particulate substance is flowed from the first sample pad (e1) with the expandable structure (j) being expanded (FIG. 11A), then the second sample pad (e2) including the conjugate pad (f) is brought into contact with the membrane (a) with the expandable structure (j) being contracted (FIG. 11b), and then a solvent such as water and a buffer is added to the second sample pad (e2) to elute the second specific binding substance to start flowing on the membrane (a).

Figure 12:
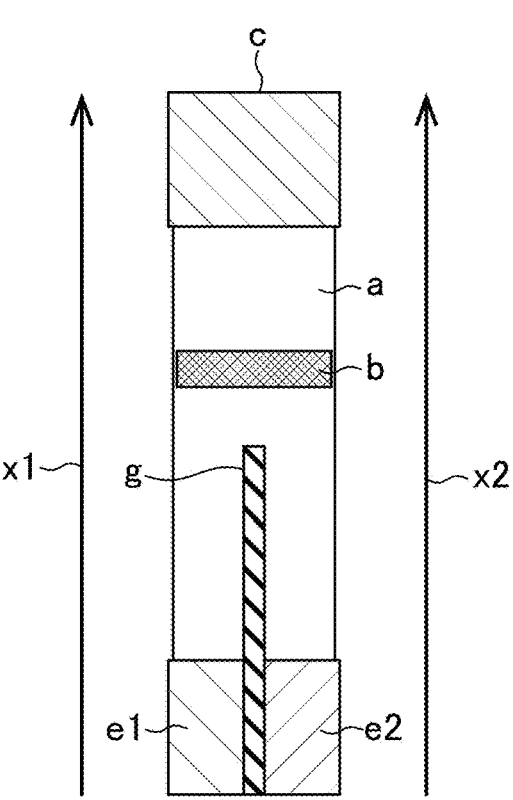
FIG. 12 shows one aspect of a test strip of the present invention for immunochromatography.
Figure 13:
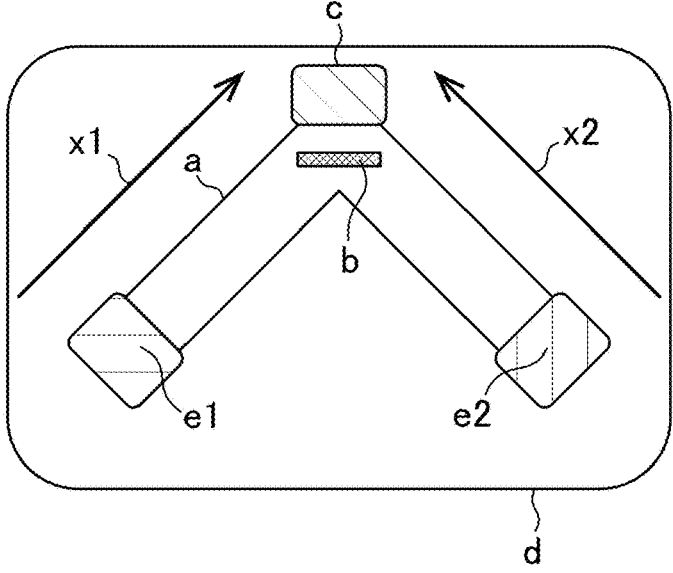
FIG. 13 shows one aspect of a test strip of the present invention for immunochromatography.

In another specific example, the test strip of the present invention for immunochromatography comprises:

a membrane (a) comprising a detection site (b) where a first specific binding substance for the first substance to be bound is immobilized;

a first sample pad (e1) contacting the membrane (a) in the upstream-side position of the detection site (b) with respect to a sample flowing direction in a first route (x1); and a second sample pad (e2) contacting the membrane in the upstream-side position of the detection site (b) with respect to a sample flowing direction in a second route (x2) which is different from the first route, wherein the second sample pad (e2) is spaced from the first sample pad (e1) (FIGS. 12 and 13), and except for the periphery of the detection site (b), the first route and the second route are spaced from each other, via a spacer (g), if necessary. In the test strip of this specific example, because a sample containing the particulate substance and a detection reagent containing a second specific binding substance (binding to a labeling substance) for the second substance to be bound can be flowed from different sample pads through different routes, the particulate substance and the second specific substance cannot be bound except for the periphery of the detection site (b), even if the detection reagent is started flowing before the sample is finished flowing completely. By doing so, as the detection reagent can be started flowing earlier, time necessary for an immunochromatography test can be shorten accordingly.

Figure 14:
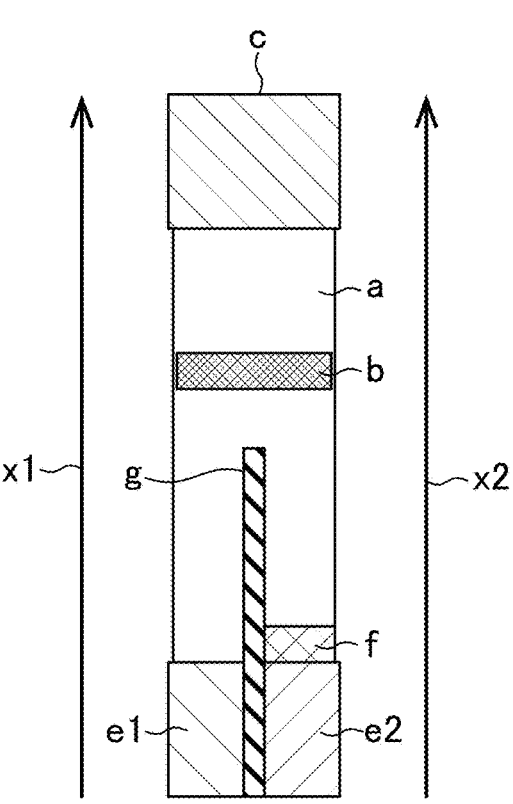
FIG. 14 shows one aspect of a test strip of the present invention for immunochromatography.
Figure 15:
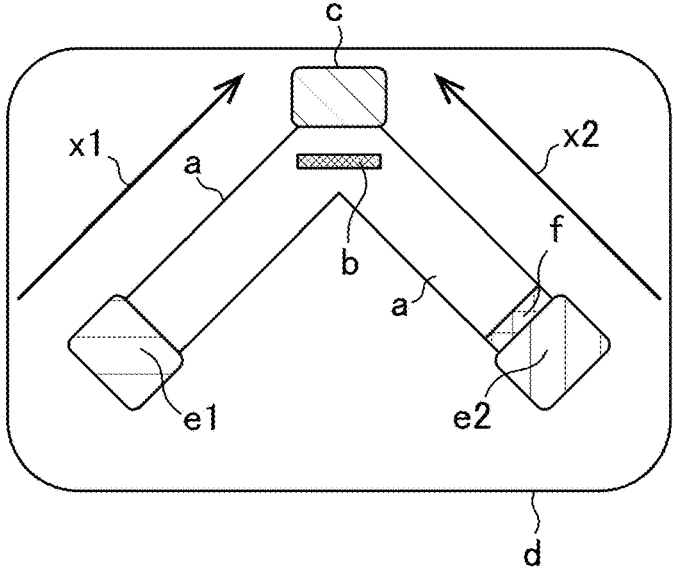
FIG. 15 shows one aspect of a test strip of the present invention for immunochromatography.

In one aspect, the second sample pad (e2) comprises a conjugate pad (f) containing the second specific binding substance (FIGS. 14 and 15). Further, in one aspect, the membrane (a) is strip-shaped, U-shaped, or V-shaped.

Figure 16:
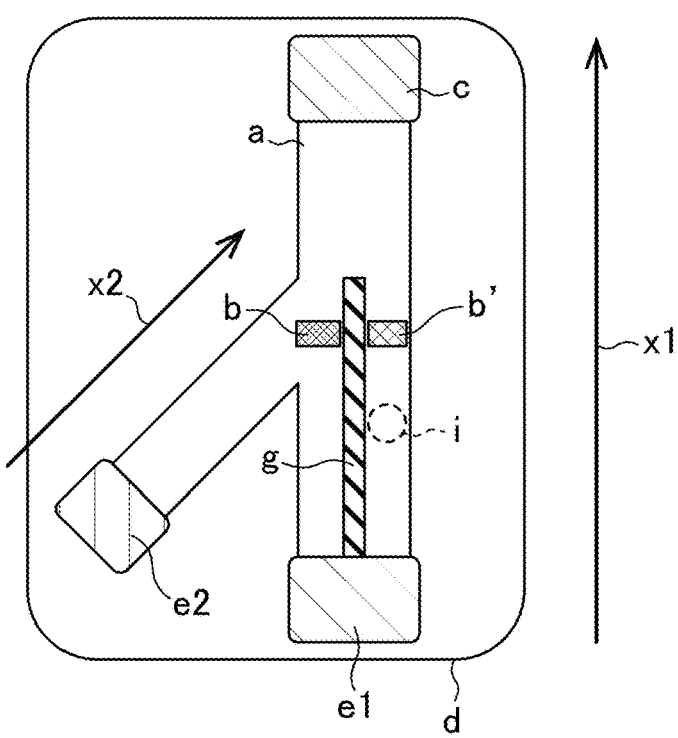
FIG. 16 shows one aspect of a test strip of the present invention for immunochromatography.

In one aspect, the particulate substance further comprises a third substance to be bound which may be the same as or different from the first substance to be bound or the second substance to be bound, wherein the membrane (a) further comprises: an additional detection site (b') where a third specific binding substance for the third substance to be bound is immobilized; and a spacer (g) arranged so as to divide the first route in the downstream-side position of the first sample pad (e1) with respect to a sample flowing direction in the first route, and wherein the detection site (b) and the additional detection site (b') are arranged in different routes which are divided by the spacer (g) (FIG. 16). The particulate substance which is flowed from the first sample pad (e1) and is captured in the detection site (b) can be labeled with a detection reagent containing the second specific binding substance which is flowed from the second sample pad (e2). And the particulate substance captured in the additional detection site (b') can be labeled by dropwisely adding the detection reagent to a drop area (i) which lies immediately above the detection site (b') or between the detection site (b') and the first sample pad (e1). When the first substance to be bound and the third substance to be bound are different, comparison of the amount of the particulate substance captured by the detection site (b) and the amount of the particulate substance captured by the additional detection site (b') allows the relative amount to be measured between the first substance to be bound and the third substance to be bound on the particulate substance in the sample.

Figure 17:
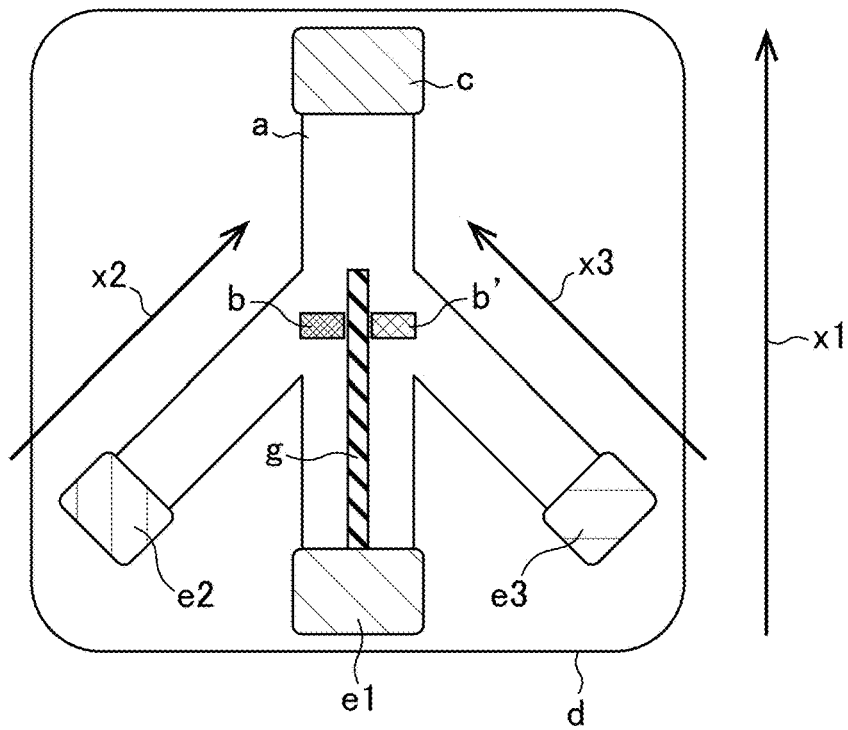
FIG. 17 shows one aspect of a test strip of the present invention for immunochromatography.
Figure 18:
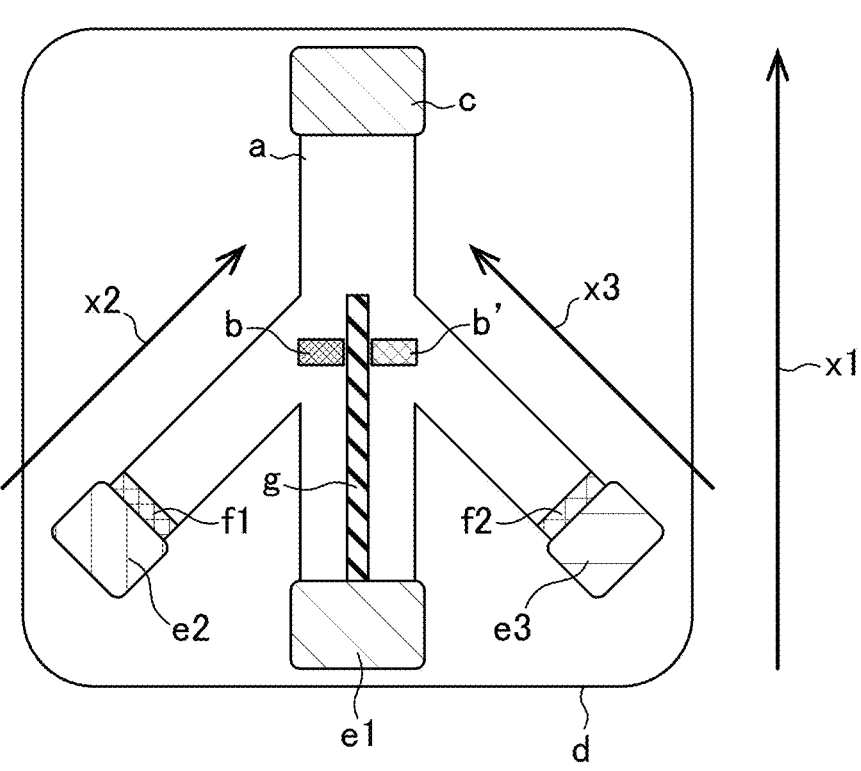
FIG. 18 shows one aspect of a test strip of the present invention for immunochromatography.

In one aspect, the test strip further includes a third sample pad (e3) contacting the membrane (a) in the upstream-side position of the additional detection site (b') with respect to a sample flowing direction in a third route (x3) which is different from the first route and the second route (FIG. 17). Further, in one aspect, the second sample pad (e2) and/or the third sample pad (e3) includes conjugate pads (f1 and f2) containing the second specific binding substance (FIG. 18).

Figure 19:
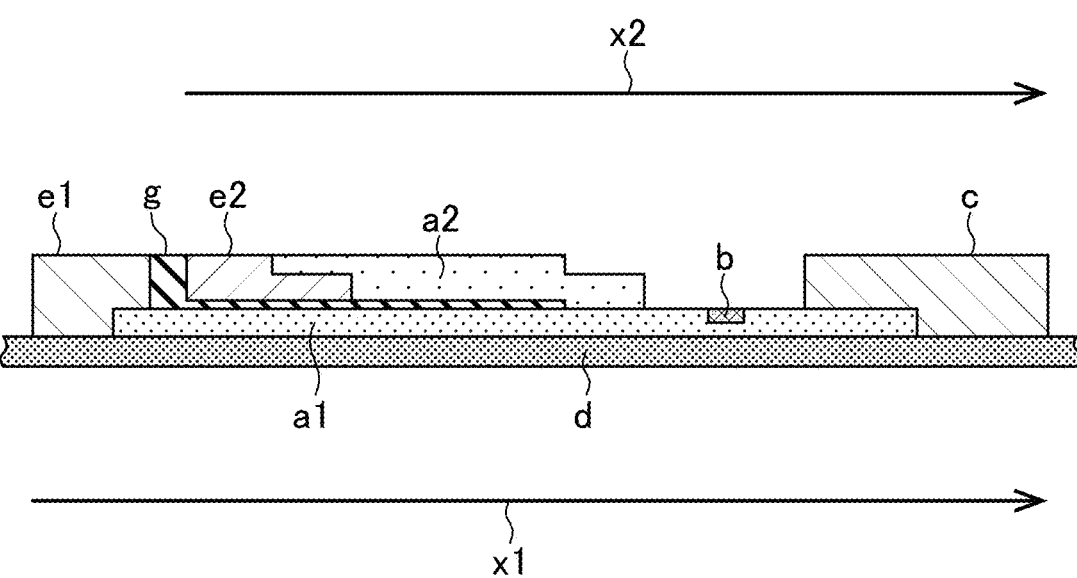
FIG. 19 shows one aspect of a test strip of the present invention for immunochromatography.
Figure 20:
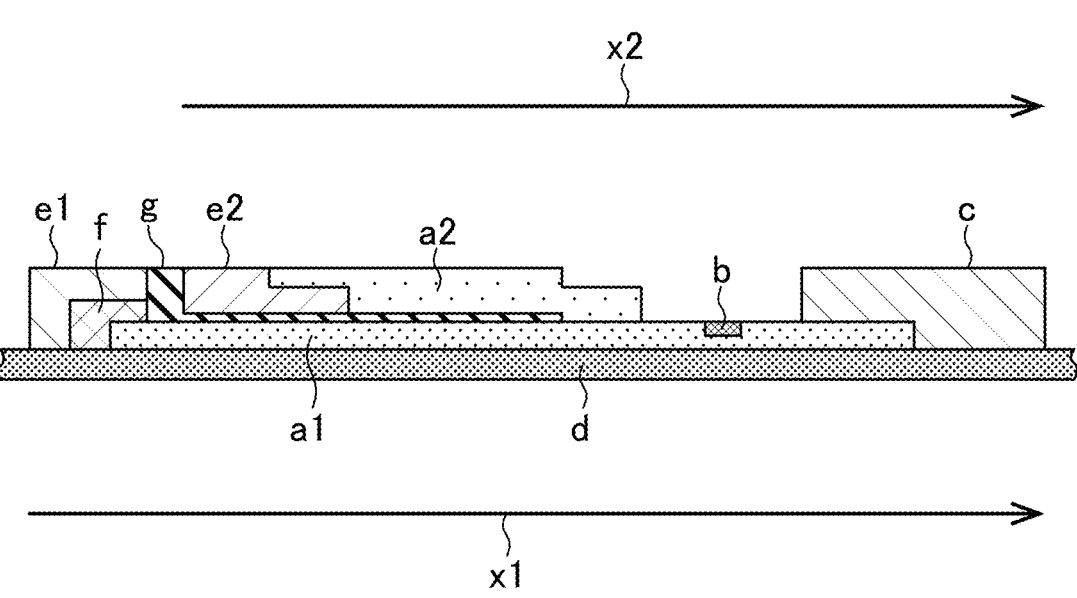
FIG. 20 shows one aspect of a test strip of the present invention for immunochromatography.

In another specific example, the test strip of the present invention for immunochromatography comprises:

a first membrane (a1) comprising a detection site (b) where a first specific binding substance for the first substance to be bound is immobilized;

a first sample pad (e1) contacting the first membrane (a1) in the upstream-side position of the detection site with respect a sample flowing direction in a first route (x1);

a second membrane (a2) contacting the first membrane (a1) between the detection site (b) and the first sample pad (e1); and a second sample pad (e2) contacting the second membrane (a2) in the upstream-side position of the detection site (b) with respect the sample flowing direction in a second route (x2) which is different from the first route, wherein the second sample pad (e2) is spaced from the first sample pad (e1) (FIG. 19). In the test strip of this specific example, one of the first sample pad (e1) or the second sample pad (e2) can be used for loading a sample containing the particulate substance, and the other can be used for loading a detection reagent containing a second specific binding substance (binding to a labeling substance) for the second substance to be bound. A sample or a detection reagent which starts flowing from the second sample pad (e2) moves to the first membrane (a1) contacting the second membrane (a2) while flowing, and reaches the detection site (b). The second membrane (a2) may contact the first membrane (a1) at its extremity area. In one aspect, either one of the first sample pad (e1) or the second sample pad (e2) includes a conjugate pad (f) containing the second specific binding substance (FIG. 20).

Figure 21:
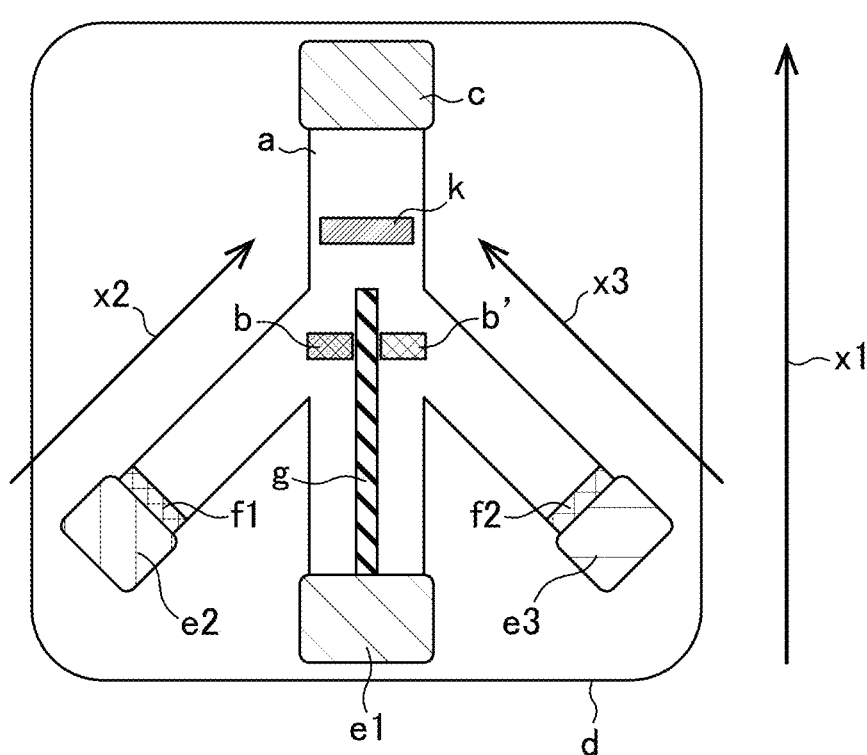
FIG. 21 shows one aspect of a test strip of the present invention for immunochromatography.

The test strip of the present invention for immunochromatography can adopt any configuration which is commonly used in the art. For example, in the test strip, the membrane may further comprise a control site which judges the success or failure of an immunochromatography test. The control site is not specifically limited, but may be a control line (k) where a substance such as an antibody that can capture the second specific binding substance (binding to a labeling substance) contained in the detection reagent is immobilized (FIG. 21), and a plurality of such a control lines may be provided depending on the type of a detection reagent used.

In the following, the present invention is specifically described using examples, but the scope of the invention is not limited to these examples.

EXAMPLES

1. Method for Preparing Exosome Solution (1) Preparation from Cell Culture Supernatant 20 mL of RPMI1640 medium containing 10% FBS (designation: Fetal Bovine Serum, manufacturer: Life Technologies), 1% PSA (designation: Penicillin-Streptomycin-Amphotericin B buffer (×100) (antibiotics-antifungal agent solution), manufacturer: Wako Pure Chemical Corporation), and 2 mM Glutamax (manufacturer: Life Technologies) was used to culture a breast cancer cell line MCF7 in a 150 mm dish up to 80% of the bottom area of the dish. After the medium was removed, the culture was washed with the 20 mL phosphate-buffered saline (PBS) twice, and 20 mL of 2 mM Glutamax-containing Advanced RPMI 1640 Medium (manufacturer: Life Technologies) was added thereto to culture it for 48 hours. A cell culture supernatant (200 mL) whose content is equivalent to that of ten 150 mm dishes was centrifuged under 2,000×g, 4° C. for 10 minutes, its supernatant was centrifuged under 10,000×g, 4° C. and the supernatant finally obtained was filtered through a filter having a pore size of 0.22 μm. The filtrate was centrifuged under 175,000×g, 4° C. for 95 minutes, and the supernatant was removed to obtain a precipitation fraction. The precipitation fraction was dispersed with 13 mL of 1× PBS and was centrifuged under 210,000×g, 4° C. for 95 minutes. After its supernatant was removed, the precipitation was dispersed with 0.2 mL of PBS again to prepare an exosome solution (E solution 1).

Also, instead of MCF7 cell, MDA-MB-231(abbreviation: MM231) which is another breast cancer cell line was used to prepare an exosome solution (E solution 2) using the same method as described above.

(2) Preparation from Serum 4 mL serum (item number: 12181201, dealer: Cosmo Bio Co., Ltd.) was centrifuged under 16,500×g, 4° C. for 20 minutes and its supernatant was filtered through a filter having a pore size of 0.22 μm. The filtrate was centrifuged under 210,000×g, 4° C. for 45 minutes, and the supernatant was removed to obtain a precipitation fraction. The precipitation fraction was dispersed with 4 mL PBS and was centrifuged under 210,000×g, 4° C. for 45 minutes. After its supernatant was removed, the precipitation was dispersed with 0.1 mL PBS again to prepare an exosome solution (E solution 3).

2. Evaluation for Cell-Derived Vesicle Solution (1) Measurement of Size and Number Concentration of Particles Each type of exosome solutions was diluted to measure the size and the number concentration of exosome particles by NanoSight nanoparticle analytical system (made by Malvern Panalytical). The result is set forth below.

[E solution 1] particle size: 147 nm, particle number concentration: $1.5 \times 10^{12}$ counts/mL

[E solution 2] particle size: 143 nm, particle number concentration: $1.9 \times 10^{12}$ counts/mL

Figure 22:
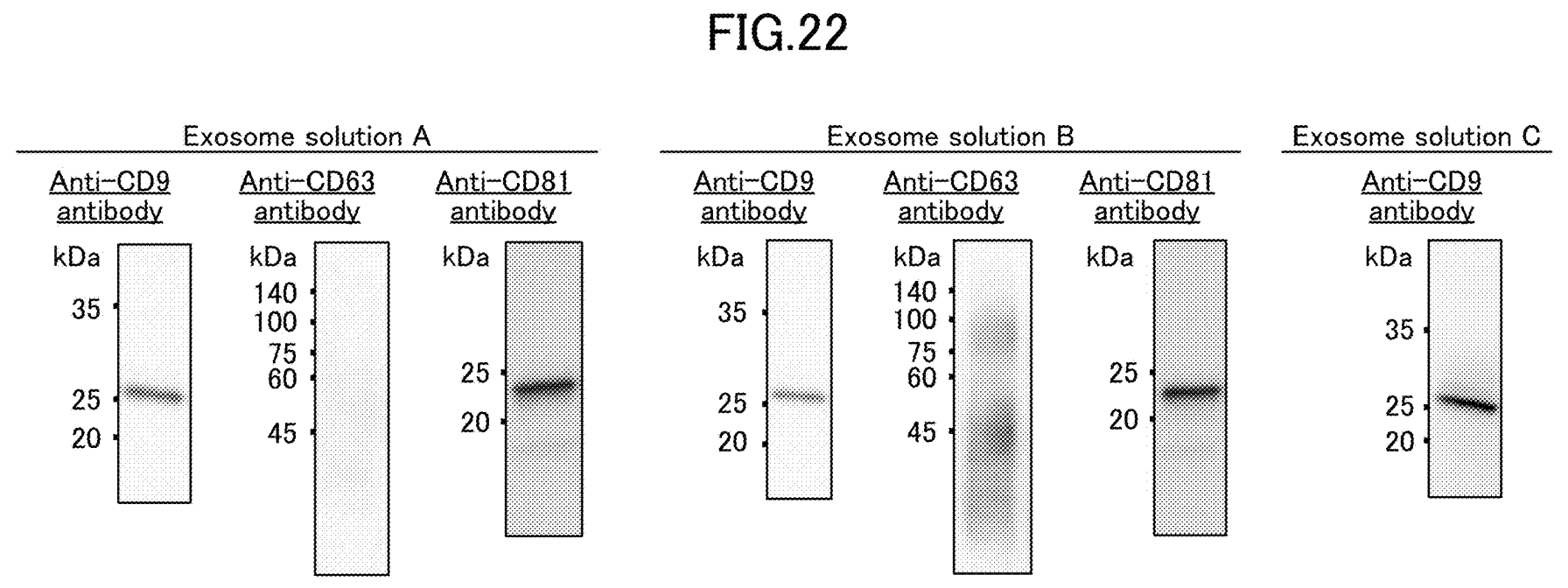

[E solution 3] particle size: 139 nm, particle number concentration: $4.9 \times 10^{10}$ counts/mL (2) Western Blotting E solutions 1 and 2 prepared so as to contain $2.5 \times 10^9$ counts of exosomes, and E solution 3 prepared so as to contain $1.3 \times 10^9$ counts of exosomes were subjected to SDS-Polyacrylamide gel electrophoresis using a sample buffer (for SDS PAGE, six-fold concentration, without a reducing agent) (item number: 09500-64, manufacturer: NACALAI TESQUE, INC.). The SDS-Polyacrylamide gel after electrophoresis was transferred to a PVDF membrane (made by Merck). The PVDF membrane after transfer was blocked by dipping into TBS-T (20 mM Tris-HCl (pH 8.0), 150 mM NaCl, 0.05% Tween®20) containing 2% skim milk. After completion of blocking, the PVDF membrane was reacted with mouse anti-CD9 antibody (made by Hansa Bio Med), mouse anti-CD63 antibody (made by Hansa Bio Med), or mouse anti-CD81 antibody (made by Hansa Bio Med) which was diluted with 0.2% skim milk-containing TBS-T. Then, after the PVDF membrane was washed with TBS-T three times, it was reacted with HRP-labeled goat anti mouse IgG antibody (made by Bio-Rad Laboratories). Finally, this PVDF membrane was washed with TBS-T three times and was dipped into ImmunoStar LD (made by Wako Pure Chemical Corporation) to detect chemiluminescence using ImageQuant LAS4000 (made by GE Healthcare) immediately thereafter to evaluate the obtained image visually or by brightness analysis. The result is shown in FIG. 22 and Table 1.

(Criteria for Visual Evaluation)

++: Band is clearly distinguishable

+: Band is distinguishable

−: Band is not distinguishable

TABLE 1

| | | | |
|---|---|---|---|
| | Result of Western blotting | | |
| | | Antibody | |
| | Anti-CD9 antibody | Anti-CD63 antibody | Anti-CD81 antibody |
| E solution 1 | ++ | − | ++ |
| E solution 2 | + | + | ++ |
| E solution 3 | ++ | (not tested) | (not tested) |

While any of CD9, CD63 and CD81 are known to be present on the surface of exosomes, the number of them are different depending on the derived cells. Because in the Western blotting in this test, it was suggested that the amount of CD63 present in exosomes in E solution 1 was a few, it is expected that the use of anti-CD63 antibody in an immunochromatography test leads to reduction in the detection sensitivity.

3. Preparation of Metal Nanoparticles (1) Gold Nanoplate Suspension

In accordance with an ordinary method, a suspension A (maximum absorption wavelength 616 nm; blue) containing a gold nanoplate (blue plate-like nanoparticles having the maximum length of 45 nm and thickness of 23 nm, abbreviation: AuPL) was prepared (see Patent Literature 4, if necessary).

(2) Spherical Gold Colloidal Suspension

Suspension B (maximum absorption wavelength 524 nm; red) containing commercially available spherical gold colloidal particles (made by BBI Solutions, particle size 40 nm, abbreviation: AuSP) was used in the subsequent experiment.

4. Preparation of Antibody-Bearing Metal Nanoparticles and Developing Solution 0.1 mL of 0.05 mg/mL of mouse anti-CD9 antibody (item number: HBM-CD9-100, manufacturer: Hansa Bio Med) solution was added to 1 mL suspension A or B whose concentration was adjusted so that the absorbance at the maximum absorption wavelength was set to 2.0, and this was stood still for one hour. Then, 0.05 mL of 0.5% polyethylene glycol (molecular weight of 20,000) aqueous solution and 0.1 mL of 2% BSA aqueous solution were added thereto to block the surface of metal nanoparticles. Subsequently, the metal nanoparticles were precipitated by a centrifuge to remove the supernatant, and were again dispersed with 1 mL of 10 mM HEPES buffer containing 150 mM sodium chloride and 1% BSA. After centrifugation operation was again performed to remove the supernatant, the metal nanoparticles were again dispersed with the same buffer to adjust the concentration so that the absorbance at the maximum absorption wavelength was set to 1. These solutions were designated as developing solutions A9 and B9 used for an immunochromatography test.

And as for suspension A, except that, instead of mouse anti-CD9 antibody, mouse anti-CD63 antibody (item number: HBM-CD63-100, manufacturer: Hansa Bio Med) or mouse anti-CD81 antibody (item number: HBM-CD81-100, manufacturer: Hansa Bio Med) was used, developing solutions A63 and A81 containing antibody-bearing metal nanoparticles were prepared in the same manner as the above-described method. The types of the metal nanoparticles and detection antibodies contained in the prepared developing solutions are shown in Table 2.

TABLE 2

| | | |
|---|---|---|
| Types of the metal nanoparticles and detection antibodies contained in the prepared developing solutions | | |
| Developing solution | Metal nanoparticle | Detection antibody |
| A9 | Gold nanoplate | Anti-CD9 antibody |
| A63 | | Anti-CD63 antibody |
| A81 | | Anti-CD81 antibody |
| B9 | Spherical gold colloid | Anti-CD9 antibody |

5. Immunochromatography Test (1) Immobilization of Capture Antibody to Immunochromatography Test Paper Mouse anti-CD9 antibody (item number: HBM-CD9-100, manufacturer: Hansa Bio Med) was diluted with PBS containing 10% sucrose so that the concentration was set to be 0.25 g/mL, and 0.75 µL of the dilution was added dropwise to the center part of immunochromatography test paper (made by ForDx, Inc.) comprising a plate-shaped nitrocellulose membrane, where to one end of the membrane, a water absorption pad has been attached, in order to immobilize the antibody on the membrane as a capture antibody. Then, 10 mL PBS containing 3% BSA was developed to block the overall membrane.

(2) Method of Present Invention

Regarding the immunochromatography test paper where the capture antibody was immobilized, its end where the water absorption pad has not been attached was dipped into a test solution containing exosomes to develop the test solution. Next, any of developing solutions described in the foregoing Table 2 was developed. Finally, the color expressed in the portion on which the capture antibody was immobilized was evaluated by any of methods described later.

(3) Conventional Method (Comparative Method)

A test solution containing exosomes was mixed with any of developing solutions described in the foregoing Table 2. Next, the mixture was developed to immunochromatography test paper on which a capture antibody was immobilized. Finally, the color expressed in the portion on which the capture antibody was immobilized was evaluated by any of methods described later.

(4) Addition of Surfactant

When a surfactant was added to an exosome solution, 5 μL surfactant solution was added to 1 μL exosome solution, and PBS containing 1% bovine serum albumin (BSA) was added thereto so that the whole amount was set to 50 μL to prepare a test solution. As the surfactant described above, 0.01% (octylphenoxy) polyethoxyethanol (designation: Nonidet™ P-40, abbreviation: NP40) solution or 0.1% Tween® 20 solution was used.

6. Method for Evaluation (1) Visual Evaluation

The judgment portion (where mouse anti-CD9 antibody has been immobilized) on the membrane of immunochromatography test paper was visually checked, and the extent of color expressed was evaluated according to the following criteria.

++: Clearly distinguishable

+: Distinguishable

+−: Slightly distinguishable

−: Indistinguishable (2) Analysis of Brightness

Immunochromatography test paper after the developing solution containing the detection antibody was developed was scanned by a scanner (device name: CanoScan LiDE500F, manufacturer: Canon Inc.), and the brightness in the judgment portion and the lowest brightness in the portion other than the judgment portion were measured by image analytical software (Image-J) to convert the detection signal into numbers. More specifically, each part was respectively measured five times and the difference between the median values of the obtained numerical values was determined. And the value when the control solution without exosomes was developed was subtracted from the value when the test solution with exosomes was developed to determine the difference in brightness as the detection signal. Meanwhile, Image-J is open-source, publicly-owned image processing software which was developed by Wayne Rasband of National Institutes of Health (http://imagej.nih.gov/ij/).

(3) Measurement by Immunochromato Reader

Immunochromatography test paper after the developing solution containing the detection antibody was developed was measured by Immunochromato reader (model number: C10066-10, manufacturer: Hamamatsu Photonics K.K.). When the gold nanoplate (blue) was used, it was measured in the blue-based color line measurement mode, and when the spherical gold colloid (red) was used, it was measured in the red-based color line measurement mode. The value when the control solution without exosomes was developed was subtracted from the value when the test solution with exosomes was developed to determine absorbance as the detection signal.

7. Comparison of Developing Methods in Immunochromatography Test

Figure 23:
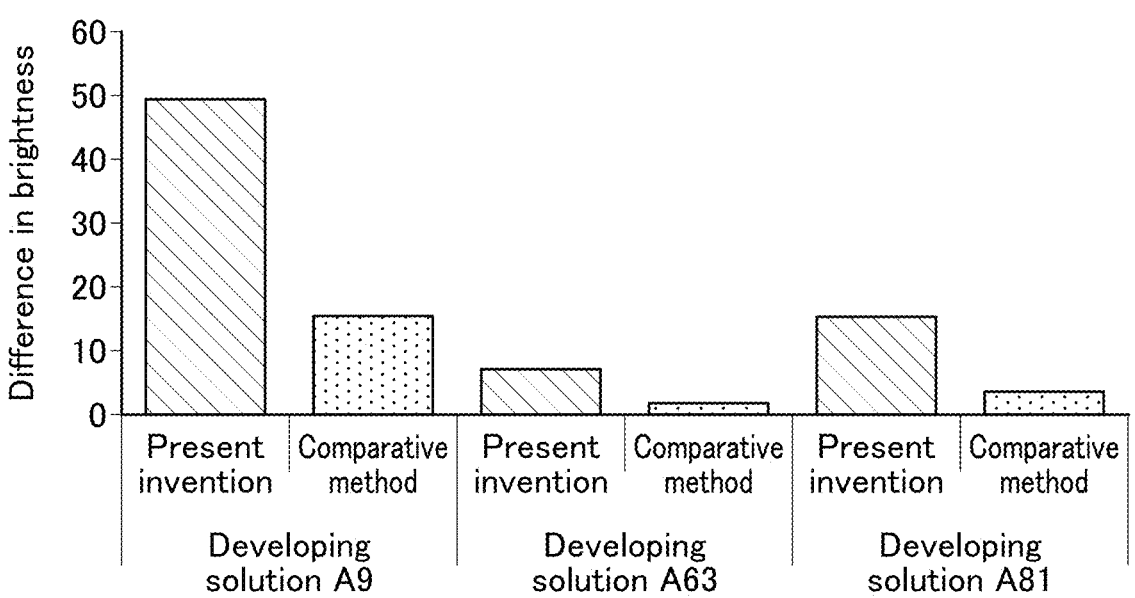
FIG. 23 shows the result of an immunochromatography test by the present invention or comparative methods.

As a test solution containing exosomes, 25 μL serum (item number: 12181201, dealer: Cosmo Bio Co., Ltd.) was used, and as a developing solution containing a detection antibody, 60 μL developing solutions A9, A63 or A81 was used. An immunochromatography test was carried out by the method of the present invention or a comparative method, and the result of visual judgment is shown in Table 3, and the analysis result of brightness is shown in FIG. 23.

TABLE 3

| | Result of visual judgment | | |
|---|---|---|---|
| Test method | Developing solution A9 | Developing solution A63 | Developing solution A81 |
| Method or the present invention | ++ | + | + |
| Comparative method | + | − | +− |

Whichever developing solution (detection antibody) was used, the detection sensitivity was improved in the case where the immunochromatography test was carried out in accordance with the method of the present invention, as compared to the comparative method. Notably, when the developing solution A63 was used, although expressed color could not be visually checked in the comparative method, it could be visually checked in the present invention.

Figure 24:
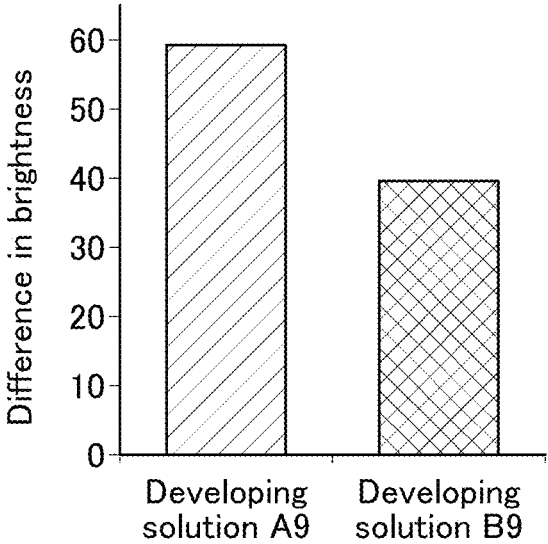
FIG. 24 shows the result of an immunochromatography test by the present invention.

8. Detection of Exosomes in Each Type of Samples (1) Cancer Cell Line-Derived Exosomes PBS containing 1% BSA was added to E solution 1 containing $5.0 \times 10^9$ counts of exosomes so that the whole amount was set to 50 μL. This was used as a test solution for an immunochromatography test, 60 μL developing solution A9 or B9 was used as a developing solution containing a detection antibody to perform an immunochromatography test in accordance with the method of the present invention. The analysis result of brightness is shown in FIG. 24.

Regardless of types of antibody-labeling metal nanoparticles, the good test result for immunochromatography could be obtained by the method of the present invention.

(2) Exosomes in Whole Blood

Figure 25:
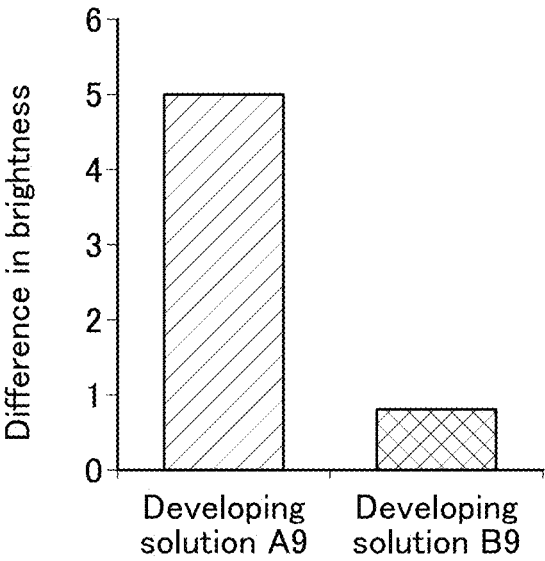
FIG. 25 shows the result of an immunochromatography test by the present invention.

50 μL of five-fold dilution in which whole blood (dealer: BizComJapan, Inc.) was diluted with PBS was used as a test solution for an immunochromatography test, and 60 μL developing solution A9 or B9 was used as a developing solution containing a detection antibody to perform an immunochromatography test according to the method of the present invention. The analysis result of brightness is shown in FIG. 25.

Even though a sample in which exosomes have not been isolated or purified was used, the good test result for immunochromatography could be obtained by the method of the present invention. Also, even when the use of spherical gold colloid as an antibody label only allowed slight difference in brightness to be measured, the use of gold nanoplate of anisotropic gold nanoparticles as an antibody label could further improve the detection sensitivity.

(3) Exosomes in Culture Supernatant

Figure 26:
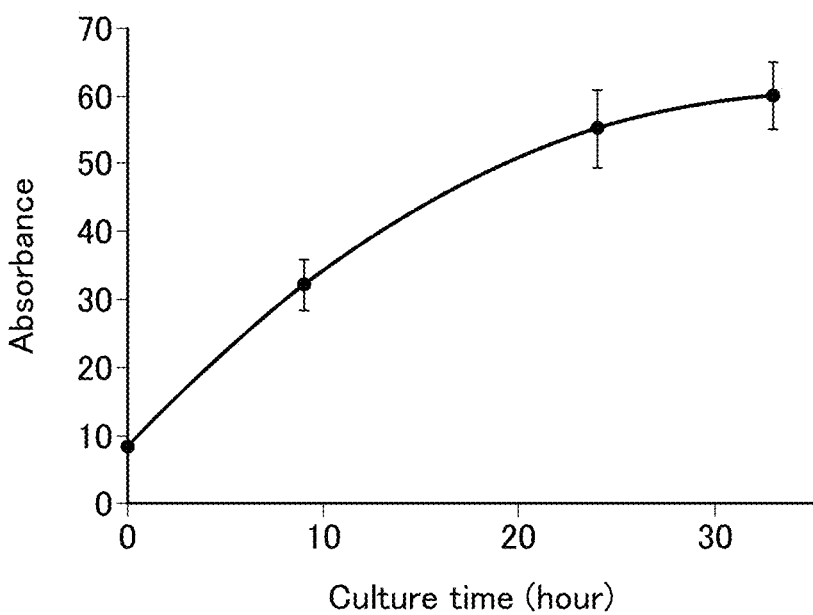
FIG. 26 shows a change in an exosome amount in a culture supernatant over time.

Breast cancer cell line MCF7 was cultured to achieve up to 80% of the bottom area of the dish, and its medium was exchanged with RPMI1640 medium without serum to collect the culture supernatant overtime. 50 μL of the collected culture supernatant was used as a test solution, and 60 μL of developing solution A9 was used as a developing solution containing a detection antibody to perform an immunochromatography test according to the method of the present invention. The analysis result of brightness is shown in FIG. 26.

According to the immunochromatography test in accordance with the method of the present invention, with the test that the culture supernatant was directly used, the situation where exosomes in the culture supernatant had increased over time could be observed easily. Meanwhile, this immunochromatography test result had closely correlated with the result of measurement by NanoSight nanoparticle analytical system.

(4) Exosomes in Sample Prepared by Using NP40 (surfactant)

Figure 27:
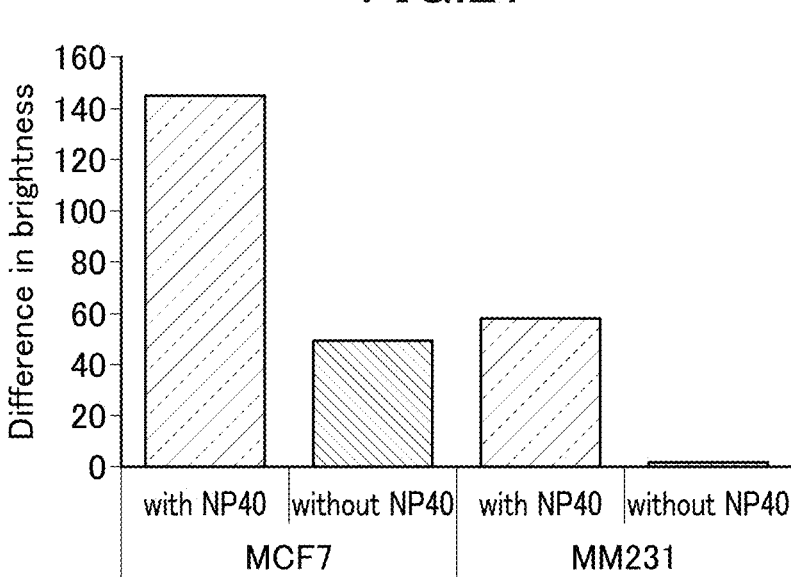
FIG. 27 shows the difference in detection sensitivity with or without addition of a surfactant.

50 µL test solution was prepared by adding or by not adding NP40 solution to E solution 1 (MCF7 cell-derived exosome solution) and E solution 2 (MM231 cell-derived exosome solution). 60 µL developing solution A9 or B9 was used as a developing solution containing a detection antibody to perform an immunochromatography test according to the method of the present invention. The analysis result of brightness is shown in FIG. 27.

By adding NP40 to the sample, any of cell-derived exosomes could improve the detection sensitivity.

(5) Exosomes in Sample Prepared by Using Tween® 20 (surfactant)

Figure 28:
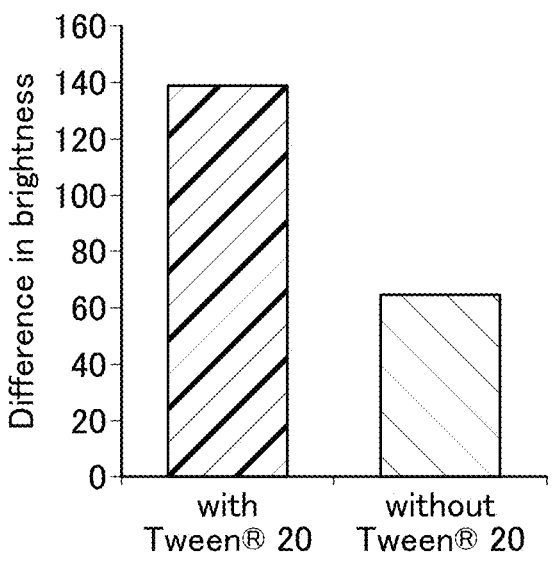
FIG. 28 shows the difference in detection sensitivity with or without addition of a surfactant.

50 µL test solution was prepared by adding or by not adding Tween® 20 solution to E solution 1 and E solution 2. 60 µL developing solution A9 was used as a developing solution containing a detection antibody to perform an immunochromatography test according to the method of the present invention. The analysis result of brightness is shown in FIG. 28.

Even when Tween® 20 was added to the sample, the detection sensitivity of exosomes could be improved as in the case of NP40 being added.

9. Quantitativeness of Immunochromatography Test

Figure 29:
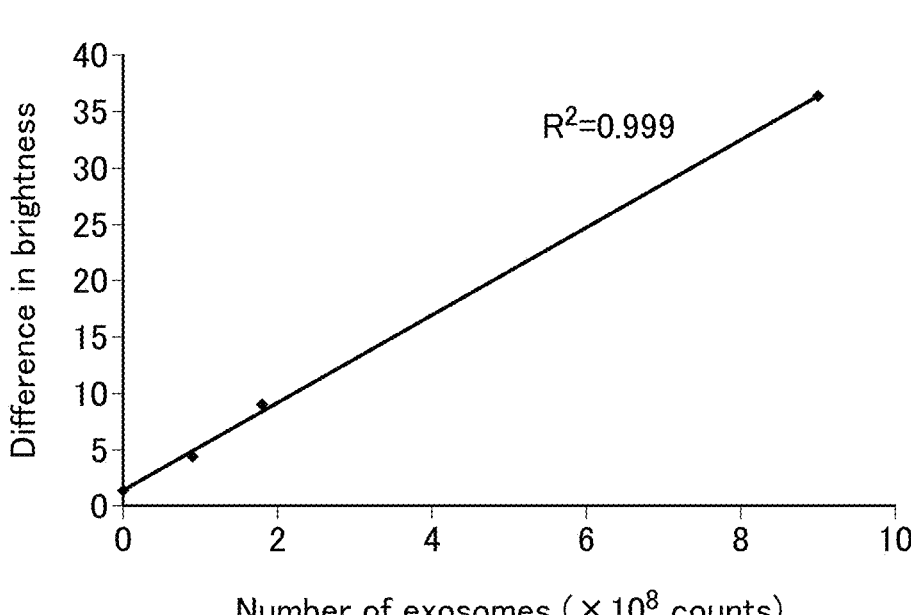
FIG. 29 shows a calibration curve created based on the difference in the measured brightness.
Figure 30:
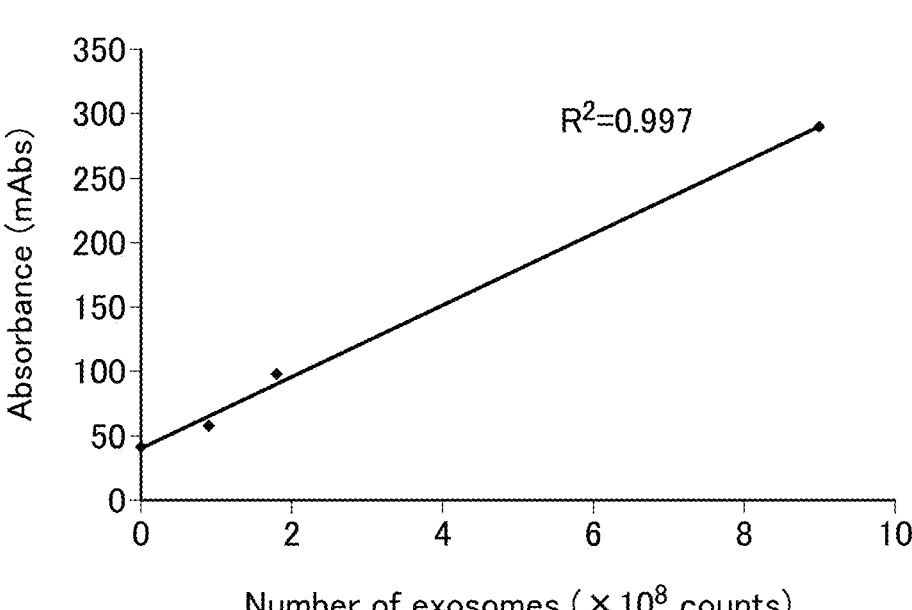
FIG. 30 shows a calibration curve created based on the measured absorbance.

Based on the result measured with NanoSight nanoparticle analytical system, E solution 1 was diluted with PBS containing 1% BSA so that the number of exosomes were set to $9.0 \times 10^8$ counts, $1.8 \times 10^8$ counts, or $0.9 \times 10^8$ counts to prepare 50 µL dilution. This dilution, or PBS containing BSA without exosomes was used as a test solution, and 60 µL developing solution A9 was used as a developing solution containing a detection antibody to perform an immunochromatography test according to the method of the present invention. The analysis result of brightness is shown in FIG. 29, and the result measured by Immunochromato reader is shown in FIG. 30.

In any of brightness analysis and measurement with Immunochromato reader, data which can draw a good calibration curve could be obtained. As a result, by performing an immunochromatography test in accordance with the present invention, a quantitative test can be carried out.

10. Comparison with Western Blotting

Based on the result measured with NanoSight nanoparticle analytical system, E solution 1 was diluted with PBS containing 1% BSA so that the number of exosomes were set to $50.0 \times 10^8$ counts, $5.0 \times 10^8$ counts, or $0.5 \times 10^8$ counts to prepare 50 µL dilution. This dilution, or PBS containing BSA without exosomes was used as a test solution, and 60 µL developing solution A9 was used as a developing solution containing a detection antibody to perform an immunochromatography test according to the method of the present invention.

Figures 31, 32:
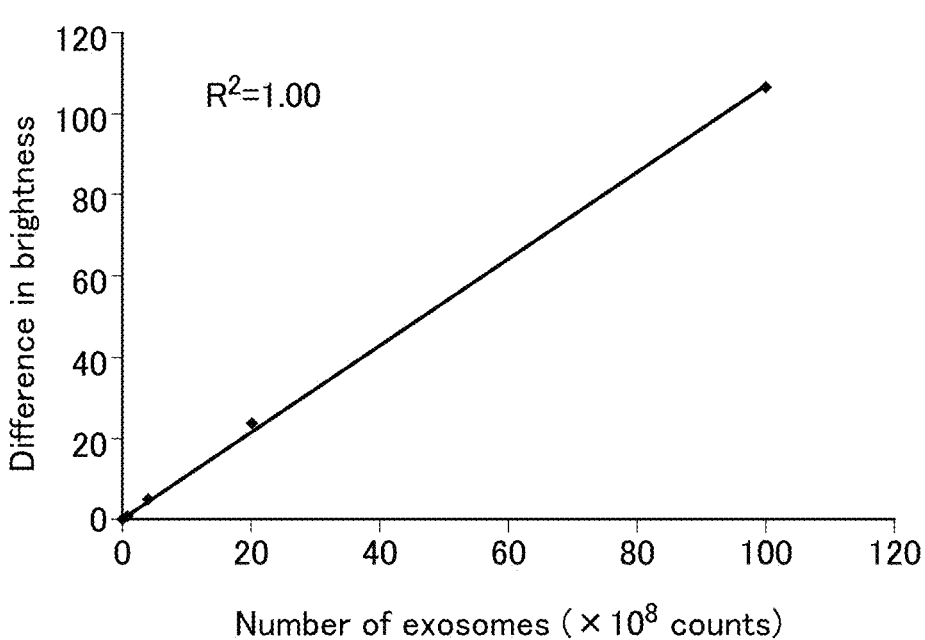
FIG. 31 shows the result of Western blotting for exosome solutions.
FIG. 32 shows a calibration curve created based on the difference in the measured brightness.

Also, the same exosome solution which was used in the immunochromatography test was analyzed with Western blotting. Mouse anti-CD9 antibody (manufacturer: Hansa Bio Med) was used as a primary antibody, and HRP labeled goat anti mouse IgG antibody (made by Bio-Rad Laboratories) was used as a secondary antibody. The result of Western blotting (photograph) is shown in FIG. 31, and the result of visual judgment for the immunochromatography test (IC) and Western blotting (WB) is shown in Table 4.

TABLE 4

| | Result of visual judgment | | | |
| --- | --- | --- | --- | --- |
| | | Exosomes ($\times 10^8$ counts) | | |
| Test method | 0 | 0.5 | 5.0 | 50.0 |
| IC | – | +– | + | ++ |
| WB | (no data) | – | +– | ++ |

While Western blotting took about eight hours to obtain the result and the operation was cumbersome, the immunochromatography test took about thirty minutes to obtain the result and the operation was easy. In addition, the detection band of the immunochromatography test in accordance with the method of the present invention was easier to visually distinguish than the detection band obtained by Western blotting. Notably, when $0.5 \times 10^8$ exosomes were used, although visual detection in Western blotting was impossible, expressed color could be visually checked in the immunochromatography test in accordance with the method of the present invention.

11. Detection by Chemiluminescence

Figure 33:
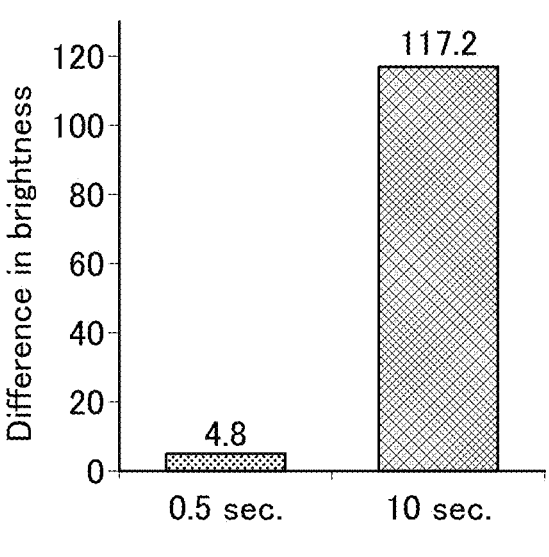
FIG. 33 shows the result of an immunochromatography test when the exposure time is changed.

Ab-10 Rapid Peroxidase Labeling Kit (made by DOJINDO LABORATORIES) was used to label mouse anti-CD9 antibody (made by Hansa Bio Med) with HRP. HRP labeled mouse anti-CD9 antibody was diluted with 10 mM HEPES buffer containing 150 mM sodium chloride and 1% BSA to prepare a developing solution having an antibody concentration of 0.2 µg/mL. Also, based on the result measured with NanoSight nanoparticle analytical system, E solution 1 was diluted with PBS containing 1% BSA so that the number of exosomes were set to $100.0 \times 10^8$ counts, $20 \times 10^8$ counts, $4 \times 10^8$ counts or $0.8 \times 10^8$ counts to prepare 50 µL dilution. This dilution, or PBS containing BSA without exosomes was used as a test solution, and 60 µL developing solution containing HRP labeled mouse anti-CD9 antibody was used to perform developing operation according to the method (item 5(2)) of the present invention. After the developing solution was developed, 50 µL of 10 mM HEPES buffer containing 150 mM sodium chloride and 1% BSA was developed, the HRP labeled mouse anti-CD9 antibody remaining in the location other than the detection site on immunochromatography test paper was washed, and then ImmunoStar LD (made by Fujifilm Wako Pure Chemical Corporation) as a chromogenic substrate was added dropwise to immunochromatography test paper. Immediately after the drop, chemiluminescence was measured by a CCD imager ImageQuant LAS 4000 (made by GE Healthcare). The analysis result of brightness of the image obtained with the exposure time of 0.5 second is shown in FIG. 32. In addition, for the case of exosome counts of $4 \times 10^8$, the result of chemiluminescence measured with the exposure time being changed is shown in FIG. 33.

Also in detection by chemiluminescence, data which can draw a good calibration curve could be obtained. As a result, by performing an immunochromatography test according to the present invention, a quantitative test can be carried out. Further, when the exposure time was changed from 0.5 second to 10 seconds, difference in brightness was increased to 24 times. In this way, for detection by chemiluminescence, the longer the exposure time is set, the more the detection intensity can be increased, and thus it is possible to detect a minute amount of particulate substance with even higher sensitivity.

As a result, we found out that a particulate substance can be detected with high sensitivity by performing immunochromatography in specific order. Therefore, this allows a particulate substance to be detected in a quick and highly sensitive manner.

REFERENCE SIGNS LIST a membrane
a1 first membrane
a2 second membrane
b detection site
b' additional detection site
c water absorption pad
d substrate
d1 first substrate
d2 second substrate
e1 first sample pad
e2 second sample pad
f conjugate pad
f1 first conjugate pad
f2 second conjugate pad
g spacer
g1 first spacer
g2 second spacer
h inhibition area
i drop area
i1 first drop area
i2 second drop area
j expandable structure
k control line
x sample flowing direction
x1 sample flowing direction in first route
x2 sample flowing direction in second route
x3 sample flowing direction in third route

The invention claimed is:

1. A method for detecting a particulate substance by immunochromatography, the particulate substance comprising, on its surface, a plurality of substances to be bound containing a first substance to be bound and a second substance to be bound which may be the same or different with respect to each other, wherein the method comprises the steps of:
    (1) contacting on a membrane of a test strip for immunochromatography a sample containing the particulate substance with a first specific binding substance for the first substance to be bound to capture the particulate substance with the first specific binding substance;
    (2) subsequently, after said capturing of the particulate substance, contacting the captured particulate substance with a second specific binding substance for the second substance to be bound to label the particulate substance; and
    (3) detecting the labeled particulate substance,
    wherein the first specific binding substance is immobilized on the membrane, and the second specific binding substance is bound to a labeling substance.

2. The method according to claim 1, wherein the particulate substance is an extracellular vesicle.

3. The method according to claim 1, wherein the labeling substance is a metal nanoparticle, a chemiluminescence substance, or a fluorescence substance.

4. The method according to claim 3, wherein the metal nanoparticle is an anisotropic metal nanoparticle.

5. The method according to claim 4, wherein the anisotropic metal nanoparticle is blue or black, and the sample contains blood.

6. The method according to claim 1, further comprising the step of adding a surfactant to the sample.

7. The method according to claim 1, wherein the first substance to be bound is the same as the second substance to be bound.

8. The method according to claim 7, wherein the binding site of the first specific binding substance in the first substance to be bound is the same as the binding site of the second specific binding substance in the second substance to be bound.

9. The method according to claim 1, wherein the detecting step comprises the step of quantifying the particulate substance.

10. The method according to claim 9, wherein the quantifying step comprises the step of measuring a labeling signal by a mass spectrometer, Immunochromato reader, or an image analyzer.

11. The method according to claim 10, wherein an ionization method of the mass spectrometer is an Inductively Coupled Plasma (ICP) method or a Matrix-Assisted Laser Desorption/Ionization (MALDI) method.

12. The method according to claim 1, which is performed by using a test strip for immunochromatography to detect a particulate substance, the particulate substance comprising, on its surface, a plurality of substances to be bound containing a first substance to be bound and a second substance to be bound which may be the same or different with respect to each other, wherein the test strip comprises:
    a membrane comprising a detection site where a first specific binding substance for the first substance to be bound is immobilized, and comprising or not comprising a control site where the success or failure of an immunochromatography test is judged; and
    a first sample pad contacting the membrane in the upstream-side position of the detection site with respect to a sample flowing direction,
    wherein no conjugate pad is included on the way from the first sample pad to the detection site.

13. The method according to claim 1, which is performed by using a test strip for immunochromatography to detect a particulate substance, the particulate substance comprising, on its surface, a plurality of substances to be bound containing a first substance to be bound and a second substance to be bound which may be the same or different with respect to each other, wherein the test strip comprises:
    a membrane comprising a detection site where a first specific binding substance for the first substance to be bound is immobilized, and comprising or not comprising a control site where the success or failure of an immunochromatography test is judged;
    a first substrate which includes a first sample pad contacting the membrane in the upstream-side position of the detection site with respect to a sample flowing direction; and
    a second substrate which includes a second sample pad,
    wherein the first substrate and the second substrate are approachable so that the second sample pad contacts the membrane in the far upstream-side position of the first sample pad with respect to the sample flowing direction.

14. The method according to claim 1, which is performed by using a test strip for immunochromatography to detect a particulate substance, the particulate substance comprising, on its surface, a plurality of substances to be bound containing a first substance to be bound and a second substance to be bound which may be the same or different with respect to each other, wherein the test strip comprises:
    a membrane comprising a detection site where a first specific binding substance for the first substance to be bound is immobilized, and comprising or not comprising a control site where the success or failure of an immunochromatography test is judged; and a first sample pad contacting the membrane in the upstream-side position of the detection site with respect to a sample flowing direction in a first route; and a second sample pad contacting the membrane in the upstream-side position of the detection site with respect to a sample flowing direction in a second route which is different from the first route, wherein the second sample pad is spaced from the first sample pad.

15. The method according to claim 14, wherein the second sample pad comprises a conjugate pad containing a second specific binding substance for the second substance to be bound, and the second specific binding substance is bound to a labeling substance.

16. The method according to claim 14, wherein the particulate substance further comprises a third substance to be bound which may be the same as or different from the first substance to be bound or the second substance to be bound, wherein the membrane further comprises: an additional detection site where a third specific binding substance for the third substance to be bound is immobilized; and a spacer arranged so as to divide the first route in the downstream-side position of the first sample pad with respect to a sample flowing direction in the first route, and wherein the detection site and the additional detection site are arranged in different routes which are divided by the spacer.

17. The method according to claim 16, further comprising a third sample pad contacting the membrane in the upstream-side position of the additional detection site with respect to a sample flowing direction in a third route which is different from the first route and the second route.

18. The method according to claim 17, wherein the second sample pad and/or the third sample pad comprises a conjugate pad containing the second specific binding substance.

19. The method according to claim 1, which is performed by using a test strip for immunochromatography to detect a particulate substance, the particulate substance comprising, on its surface, a plurality of substances to be bound containing a first substance to be bound and a second substance to be bound which may be the same or different with respect to each other, wherein the test strip comprises:

a first membrane comprising a detection site where a first specific binding substance for the first substance to be bound is immobilized, and comprising or not comprising a control site where the success or failure of an immunochromatography test is judged;

a first sample pad contacting the first membrane in the upstream-side position of the detection site with respect to a sample flowing direction in a first route;

a second membrane contacting the first membrane between the detection site and the first sample pad; and a second sample pad contacting the second membrane in the upstream-side position of the detection site with respect to a sample flowing direction in a second route which is different from the first route, wherein the second sample pad is spaced from the first sample pad.

20. The method according to claim 1, wherein the second specific binding substance labels the particulate substance without substantially inhibiting binding to said first specific binding substance.

* * * * *